United States Patent
Dahl et al.

(10) Patent No.: US 6,812,371 B2
(45) Date of Patent: Nov. 2, 2004

(54) COMPOSITIONS COMPRISING NONAMANTANES AND PROCESSES FOR THEIR SEPARATION

(75) Inventors: Jeremy E. Dahl, Palo Alto, CA (US); Robert M. Carlson, Petaluma, CA (US)

(73) Assignee: Chevron U.S.A. Inc., San Ramon, CA (US)

(*) Notice: Subject to any disclaimer, the term of this patent is extended or adjusted under 35 U.S.C. 154(b) by 373 days.

(21) Appl. No.: 10/012,709

(22) Filed: Dec. 12, 2001

(65) Prior Publication Data

US 2003/0100808 A1 May 29, 2003

Related U.S. Application Data

(60) Provisional application No. 60/348,355, filed on Oct. 19, 2001, and provisional application No. 60/262,842, filed on Jan. 19, 2001.

(51) Int. Cl.$^7$ .............................. C07C 13/28; C07C 7/00
(52) U.S. Cl. ........................... 585/352; 585/16; 585/21; 585/800; 585/802; 585/803; 117/68; 117/69; 117/70
(58) Field of Search ............................. 585/803, 21, 16, 585/800, 352, 802; 117/68, 69, 70

(56) References Cited

U.S. PATENT DOCUMENTS

| | | |
|---|---|---|
| 3,457,318 A | 7/1969 | Capaldi |
| 3,832,332 A | 8/1974 | Thompson |
| 4,952,748 A | 8/1990 | Alexander |
| 4,952,749 A | 8/1990 | Alexander |
| 4,952,757 A | 8/1990 | Alexander |
| 4,982,049 A | 1/1991 | Alexander |
| 5,017,734 A | 5/1991 | Baum |
| 5,019,665 A | 5/1991 | Partridge |
| 5,126,274 A * | 6/1992 | McIver et al. ............... 436/140 |
| 5,245,104 A | 9/1993 | Cullick |
| 5,268,513 A | 12/1993 | Shen |
| 5,298,666 A | 3/1994 | Shen |
| 5,306,851 A | 4/1994 | Wu |
| 5,334,228 A * | 8/1994 | Ashjian et al. ............... 44/347 |
| 5,347,063 A | 9/1994 | Shen |
| 5,369,213 A | 11/1994 | Shen |
| 5,380,947 A | 1/1995 | Chen |
| 5,382,684 A | 1/1995 | Moini |
| 5,397,488 A | 3/1995 | Chen |
| 5,410,092 A | 4/1995 | Shen |
| 5,414,189 A * | 5/1995 | Chen et al. ............... 585/801 |
| 5,430,193 A | 7/1995 | Shen |
| 5,461,184 A | 10/1995 | Swanson |
| 5,498,812 A | 3/1996 | Bradway |
| 5,576,355 A | 11/1996 | Chen |
| 6,235,851 B1 | 5/2001 | Ishii |

FOREIGN PATENT DOCUMENTS

| | | |
|---|---|---|
| EP | 0399851 | 11/1996 |
| WO | WO 95/11472 | 4/1995 |

OTHER PUBLICATIONS

Aczel, et al., "Stability of Adamantane and its Derivatives to Coal–liquefaction Conditions, and its implications toward the organic structure of Coal", *Fuel,* vol. 58, pp. 228–230, (Mar. 1979).

Balaban, et al., Systemic Classification and Nomenclature of Diamond Hydrocarbons–I, *Tetrahedron,* 34, pp. 3599–3606, (1978) no month.

Badziag, P., et al., "Nanometre–sized Diamonds are More Stable than Graphite", *Nature,* vol. 343, pp. 244–245, and 517 (Jan. 1990).

Bagrii, Ye, et al., "Catalytic Breakdown of Paraffinic Hydrocarbons in the Presence of Adamantanes", *Petrol. Chem. USSR,* vol. 30, No. 2, pp. 131–134, (1990) no month.

Chung, et al., Recent Development in High–Energy Density Liquid Fuels, *Energy and Fuels,* 13, pp. 641–649, (1999) no month.

Dahl, J., et al., Diamondoid Hydrocarbons as Indicators of Natural Oil Cracking, *Nature,* 399, pp. 54–57, (1999) no month.

Drexler, Eric K., *Nanosystems: Molecular Machinery Manufacturing and Computation,* John Wiley & Sons, pp. 238–249, (1992) no month.

Fort, Jr., et al., Adamantane: Consequences of the Diamondoid Structure, *Chem. Rev.,* 64, pp. 277–300, (1964) no month.

Hala, V.S., et al., "Analyse Unds erwendung on Pyrolyseol", *Jahrgang,* pp. 85–87, (Feb. 1971) In German–English Abstract on page 85. Considered to Extent of Abstract.

Landa, S., "Adamantane and its Homologues", *Current Science,* Gangalore, India, Vo. 32, pp. 485–489 (1963) no month.

Lin, et al., Natrual Occurrence of Tetramantane ($C_{22}H_{36}$), Pentamantane ($C_{26}H_{32}$), and Hexamantane ($C_{30}H_{36}$) in a Deep Petroleum Reservoir, *Fuel,* 74:10, pp. 1512–1521, (1995) no month.

McKervey, Synthetic Approaches to Large Diamondoid Hydrocarbonds, *Tetrahedron,* 36, pp. 971–992, (1980) no month.

Machacek, V., et al., "Let Od Objeveni Adamantanu", *Chemicke Listy/svazek,* pp. 753–761, (1982) Russian—English Abstract on p. 761. considered to extent of abstract no month.

Oya, A, et al., "Carbonization of Adamantanes to a Graphitizable Carbon", *Fuel,* vol. 60, pp. 667–669, (Aug. 1981).

(List continued on next page.)

Primary Examiner—Elizabeth D. Wood
(74) Attorney, Agent, or Firm—Burns Doane Swecker & Mathis L.L.P.

(57) ABSTRACT

Disclosed are compositions comprising one or more nonamantanes. Specifically disclosed are compositions comprising 25 to 100 weight percent of one or more nonamantanes. Also disclosed are novel processes for the separation and isolation of nonamantane components into recoverable fractions from a feedstock containing at least a higher diamondoid component which contains one or more nonamantane components.

40 Claims, 31 Drawing Sheets

OTHER PUBLICATIONS

Petrov, A., "Hydrocarbons of Adamantane Series as Indicies of Petroleum Catagenesis Process", *Advances in Organic Geo Chemistry, 6th* International Meeting on Organic Geochemistry, pp. 517–522 (1973). no month.

Prusova, D., Liquid Chromatography of Adamantanes and Carbon Adsorbents, *J. Chrom,* 234, pp. 1–11, (1982). no month.

Rollman, L., et al., "Adamantanes From Petroleum, with Zeolites", American Chemical Study, 210th ACS National Meeting, Abstract and paper, Aug. 20, 1995) .

Sandia National Laboratories (2000), World's First Diamond Micromachines Created at Sandia, Press Release, (Feb. 22, 2000), www.Sandia.gov.

Schleyer, P., et al., "Nonacyclo[11.7.1.1$^{2,18}$.0$^{3,16}$.0$^{4,13}$.0$^{5,10}$.0$^{6,14}$.0$^{7,11}$.0$^{15,20}$]–Docosane, a Bastard Tetramantane", *J. of the Am. Chem. Soc.,* 90;8, letter to the editor, Aug. 28, 1968.

Shen, M., et al., Finite $T_d$ Symmetry Models for Diamond: From Adamantane to Superadamantane ($C_{35}H_{36}$), *J. Am., Chem. Soc.,* vol. 114, No. 2, pp 497–505, (1992). no month.

Supryadkina, NY, et al., "Catalytic Dealkylation of Alkyladamantanes", *Petrol. Chem., USSR,* vol. 28, No. 2, pp. 103–110, (1988) no month.

Tominaga, K., et al., "Next–generation Fine Chemicals Raw Material–Adamantane", *Chem Econ & Eng. Review.* vol. 17, No. 10, pp. 23–29, (Oct. 1985).

Vodicka, L, et al., "High Performance Liquid Chromatography of Halogeno Derivatives of Adamantane and Diamantane", *J. Chrom,* 270, pp. 199–205, (1983). no month.

Wingert, W., "G.c.–m.s. Analysis of Diamondoid Hydrocarbons in Smackover Petroleums", *Fuel,* vol. 71, pp. 37–42, (Jan. 1992).

\* cited by examiner

Example of Symmetrical
Nonamantanes
[121(2)32(1)3]

Examples Enantiomeric
Nonamantanes

*

[121(2,3)421] Nonamantane

* Mirror plane indicating enantiomeric pair

GC Time (min.)→

A)

Hexamantanes & Heptamantanes

Parr Reaction No. 5, Product from FSL 8691, Fraction #7

Nonamantanes

B)

Starting Material FSL 8691, Fraction #7

GC Time (min.) →

A)

B)

A)

B)

A

B

Heptamantane #1 Crystals

Heptamantane #2
Crystals

A)

Total Ion Chromatogram
TIC: C17461.D

HPLC 34
Fraction #2

GCMS Time (min.) -->

*Alkyloctamantane
+ Diamantane dimer

B)

m/z-->

A)

Crystal of Nonamantane (Mol. Wt. 498)

B)

A)

B)

[12342142] Nonamantane

Formula: $C_{34}H_{36}$
Molecular Weight 444.662
Molecular Weight (Exact) 444.2817013

Carbon Framework

CPK Representation

[12342142] Nonamantane
View into Specified Diamond Crystal Lattice Plane 111　　　　　110　　　　　100

[12123121] Nonamantane

Formula: $C_{37}H_{40}$
Molecular Weight: 484.727
Molecular Weight (Exact): 484.3130015

Carbon Framework

CPK Representation

[12123121] Nonamantane
View into Specified Diamond Crystal Lattice Plane

[121(2)32(1)3] Nonamantane

Formula: $C_{38}H_{42}$
Molecular Weight 498.754
Molecular Weight (Exact) 498.3286516

Carbon Framework

CPK Representation

[121(2)32(1)3] Nonamantane
View into Specified Diamond Crystal Lattice Plane

[121324(2)3] Nonamantane

Formula: $C_{40}H_{44}$
Molecular Weight 524.792
Molecular Weight (Exact) 524.3443016

Carbon Framework

CPK Representation

[121324(2)3] Nonamantane
View into Specified Diamond Crystal Lattice Plane 111  110  100

[1212(1)3(1)4] Nonamantane

Formula: $C_{41}H_{46}$
Molecular Weight 538.819
Molecular Weight (Exact) 538.3599517

Carbon Framework

CPK Representation

[1212(1)3(1)4] Nonamantane
View into Specified Diamond Crystal Lattice Plane 111 110 100

[12121212] Nonamantane

Formula: $C_{42}H_{48}$
Molecular Weight: 552.846
Molecular Weight (Exact): 552.3756018

Carbon Framework

CPK Representation

[12121212] Nonamantane
View into Specified Diamond Crystal Lattice Plane 111  110  100

COMPOSITIONS COMPRISING NONAMANTANES AND PROCESSES FOR THEIR SEPARATION

REFERENCE TO RELATED APPLICATIONS

This application claims priority under 35 U.S.C. §119(e) to U.S. Provisional Application Ser. No. 60/262,842, filed Jan. 19, 2001 and to U.S. Provisional Application Ser. No. 60/348,355, filed Oct. 19, 2001, under both of which are incorporated by reference.

BACKGROUND OF THE INVENTION

1. Field of the Invention

This invention is directed to novel compositions comprising one or more nonamantanes. This invention is also directed to novel processes for the separation and isolation of nonamantane components into recoverable fractions from a feedstock containing one or more nonamantane components.

References

The following publications and patents are cited in this application as superscript numbers:

[1] Lin, et al., Natural Occurrence of Tetramantane ($C_{22}H_{28}$), Pentamantane ($C_{26}H_{32}$) and Hexamantane ($C_{30}H_{36}$) in a Deep Petroleum Reservoir, Fuel, 74(10):1512–1521 (1995)

[2] Alexander, et al., Purification of Hydrocarbonaceous Fractions, U.S. Pat. No. 4,952,748, issued Aug. 28, 1990

[3] McKervey, Synthetic Approaches to Large Diamondoid Hydrocarbons, Tetrahedron, 36:971–992 (1980).

[4] Wu, et al., High Viscosity Index Lubricant Fluid, U.S. Pat. No. 5,306,851, issued Apr. 26, 1994.

[5] Chung et al., Recent Development in High-Energy Density Liquid Fuels, Energy and Fuels, 1.3, 641–649 (1999).

[6] Sandia National Laboratories (2000), World's First Diamond Micromachines Created at Sandia, Press Release, (2/2212000) www.Sandia.pov.

[7] Balaban et al., Systematic Classification and Nomenclature of Diamondoid Hydrocarbons-I, Tetrahedron. 34, 3599–3606 (1978).

[8] Chen, et al., Isolation of High Purity Diamondoid Fractions and Components, U.S. Pat. No. 5,414,189 issued May 9, 1995.

All of the above publications and patents are herein incorporated by reference in their entirety to the same extent as if each individual publication or patent was specifically and individually indicated to be incorporated by reference in its entirety.

2. State of the Art

Nonamantanes are bridged-ring cycloalkanes. They are the face-fused nonamers of adamantane (tricyclo[3.3.1.1$^{3,7}$] decane) or $C_{10}H_{16}$. The compounds have a "diamondoid" topology, which means their carbon atom arrangement is superimposable on a fragment of the diamond lattice (FIG. 1). Nonamantanes possess nine of the "diamond crystal units" and therefore, it is postulated that there are hundreds of possible nonamantane structures which exist in different molecular weight families of possible structures. Among the core structures there are six families of nonamantanes having the following molecular formulas: $C_{42}H_{48}$ (molecular weight 552), $C_{41}H_{46}$ (molecular weight 538), $C_{40}H_{44}$ (molecular weight 524), $C_{38}H_{42}$ (molecular weight 498), $C_{37}H_{40}$ (molecular weight 484) and $C_{34}H_{36}$ (molecular weight 444).

Little or no published work is available for nonamantanes and higher molecular weight diamondoids. Nonamantane compounds have not been artificially synthesized or isolated and these higher diamondoids along with hexamantane, heptamantane and octamantane compounds have been recently thought only to have a theoretical existence.[7] Academic chemists have primarily focused research on the interplay between physical and chemical properties in lower diamondoids such as adamantane, diamantane and triamantane. Adamantane and diamantane, for instance, have been studied to elucidate structure-activity relationships in carbocations and radicals.[3] Process engineers have directed efforts toward removing lower diamondoids from hydrocarbon gas streams.[2] These compounds cause problems during the production of natural gas by solidifying in pipes and other pieces of equipment.

The literature contains little information regarding practical applications of higher diamondoids and even less, if any, information regarding nonamantanes. This fact is probably due to extreme difficulties encountered in their isolation and due to failed synthesis attempts. Lin and Wilk, for example, discuss the possible presence of pentamantanes in a gas condensate and further postulate that hexamantane may also be present.[1] The researchers postulate the existence of these compounds contained within petroleum solely based on a mass spectrometric selected ion monitoring (SIM) and mass spectral fragmentation patterns. They did not, however, report the isolation of a single pentamantane or hexamantane nor mention heptamantane, octamantane or nonamantane. Nor were they able to separate non-ionized components during their spectral analysis. McKervey et al. discuss an extremely low-yielding synthesis of anti-tetramantane.[3] The procedure involves complex starting materials and employs drastic reaction conditions (e.g., gas phase on platinum at 360° C.). Although one isomer of tetramantane, i.e. anti-, has been synthesized through a double homologation route, these syntheses are quite complex reactions with large organic molecules in the gas phase and have not led to the successful synthesis of other tetramantanes. Similar attempts using preferred ring starting materials in accordance with the homologation route, have likewise failed in the synthesis of pentamantanes. Likewise, attempts using carbocation rearrangement routes employing Lewis acid catalysts, useful in synthesizing triamantane and lower diamondoids have been unsuccessful in synthesizing other tetramantanes or pentamantanes. No attempt to synthesize or isolate nonamantanes has been reported.

Among other properties, diamondoids have by far the most thermodynamically stable structures of all possible hydrocarbons that possess their molecular formulas due to the fact that diamondoids have the same internal "crystalline lattice" structure as diamonds. It is well established that diamonds exhibit extremely high tensile strength, extremely low chemical reactivity, electrical resistivity greater than aluminum trioxide ($Al_2O_3$), excellent thermal conductivity, and superb optical properties.

In addition, based on theoretical considerations, the nonamantanes have sizes in the nanometer range and, in view of the properties noted above, the inventors contemplate that such compounds would have utility in micro- and molecular-electronics and nanotechnology applications. In particular, the rigidity, strength, stability, variety of structural forms and multiple attachment sites shown by these molecules makes possible accurate construction of robust, durable, precision devices with nanometer dimensions. The various nonamantanes are three-dimensional nanometer sized units showing different diamond lattice arrangements. This translates into a variety of rigid shapes and sizes for the nonamantane components. For example, [12121212] nonamantane is rod shaped, [121(2)32(1)3] nonamantane is triangular shaped, while [12342142] is an "L"-shaped structure. A variety of other shapes exist among the nonamantanes which may serve in applications which depend upon specific geometries. It has been estimated that MicroElectroMechanical Systems (MEMs) constructed out of diamond should last 10,000 times longer then current polysilicon MEMs, and diamond is chemically benign and would not promote allergic reactions in biomedical applications.[6] Again, the inventors contemplate that the various nonamantanes would have similar attractive properties. Furthermore, many of the nonamantanes would possess chirality, offering opportunities for making nanotechnology objects of great structural specificity and ones which have useful optical properties. FIG. 2 illustrates examples of symmetric and asymmetric nonamantane structures. Applications of these nonamantanes include molecular electronics, photonics and production of nonmechanical devices, and other materials.

Notwithstanding these advantages of nonamantanes, the art, as noted above, fails to provide for compositions comprising nonamantanes or for processes that would lead to these compositions. In view of the above, there is an ongoing need in the art to provide for compositions comprising one or more nonamantanes.

SUMMARY OF THE INVENTION

This invention is directed to novel compositions comprising one or more nonamantane components.

Accordingly, in one of its composition aspects, this invention is directed to a composition comprising one or more nonamantane components wherein said composition comprises at least about 25 weight percent nonamantane components based on the total weight of the diamondoids in the composition.

In another of its composition aspects, the compositions preferably comprise one or more nonamantane components wherein the nonamantane components make up from about 50 to 100 weight percent, preferably about 70 to I00 weight percent, more preferably about 90 to 100 weight percent and even more preferably about 95 to 100 weight percent of the total weight of the diamondoids in the compositions.

In another of its composition aspects, the compositions comprise at least about 10 weight percent and preferably at least about 20 weight percent of nonamantanes based on the total weight of the composition. Other compositions of this invention contain from 50 to 100 weight percent, 70 to 100 weight percent, 95 to 100 weight percent and 99 to 100 weight percent of nonamantanes based on the total weight of the composition.

In another of its composition aspects, the compositions preferably comprise from about 70 to 100 weight percent, more preferably from about 90 to I 00 weight percent, even more preferably from about 95 to 100 weight percent and most preferably from about 99 to 100 weight percent of a single nonamantane component, including isolated optical isomers thereof, based on the total weight of the composition This invention is also directed to novel processes for the separation and isolation of nonamantane components into recoverable fractions from a feedstock containing one or more nonamantane components and nonnonamantane materials. These processes for recovering a composition enriched in nonamantane components entail removing at least a portion of the nonnonamantane materials which have a boiling point below the lowest boiling nonamantane component and utilizing a subsequent separation technique to recover nonamantane components from the resulting residue. Accordingly, this aspect is directed to processes which comprise:

a) selecting a feedstock comprising recoverable amounts of nonamantane components and nonnonamantane materials;

b) removing from the feedstock a sufficient amount of nonnonamantane materials that have boiling points below the boiling point of the lowest boiling point nonamantane component in the feedstock under conditions to form a treated feedstock enriched in nonamantane components which can be recovered;

c) recovering nonamantane components by separating said treated feedstock formed in b) above with one or more additional separation techniques selected from the group consisting of chromatographic techniques, thermal diffusion techniques, zone refining, progressive recrystallization and size separation techniques.

In a preferred embodiment, after the step recited in b) the treated feedstock can be thermally treated to pyrolyze at least a sufficient amount of nondiamondoid components therefrom under conditions to provide a thermally treated feedstock retaining recoverable amounts of nonamantane. Such a pyrolization step prior to step c) is useful for thermally degrading at least a portion of any materials remaining in the treated feedstock having a thermal stability lower than the nonamantane components. This pyrolysis step can be carried out before step b) if desired.

In a preferred embodiment of this invention, directed to the chromatographic techniques, is employing high performance liquid chromatography using one or more columns, more preferably reverse phase. A more preferred method, is using columns exhibiting a different selectivity to the nonamantane components slated for enrichment. Alternatively, high performance liquid chromatography can be coupled with gas chromatography, such as preparative gas chromatography to further facilitate isolations.

BRIEF DESCRIPTION OF THE DRAWINGS

FIG. 1 illustrates the correlation of the structures of diamondoids to subunits of the diamond crystal lattice.

FIG. 10B illustrates the GC of Feedstock B atmospheric distillation fraction #7, which was used as feedstock in pyrolytic processing. FIG. 10A illustrates the GC of the product of the pyrolytic process.

FIG. 12A, shows the first column cuts containing two of the heptamantanes from Feedstock B. FIG. 12B, shows the second column peaks isolated and sent to the traps. From this procedure pure heptamantanes were isolated (FIG.'s 13–16), heptamantane #1, the first heptamantane to elute in our GC/MS assay, and heptamantane #2 which is the second to elute. This same methodology can be used to separate nonamantanes using HPLC fractions (e.g. FIG. 11) as a starting material.

DETAILED DESCRIPTION OF THE INVENTION

This invention is directed to compositions comprising one or more nonamantane components. However, prior to describing this invention in further detail, the following terms will first be defined.

Definitions

As used herein, the following terms have the following meanings.

Figure 1:
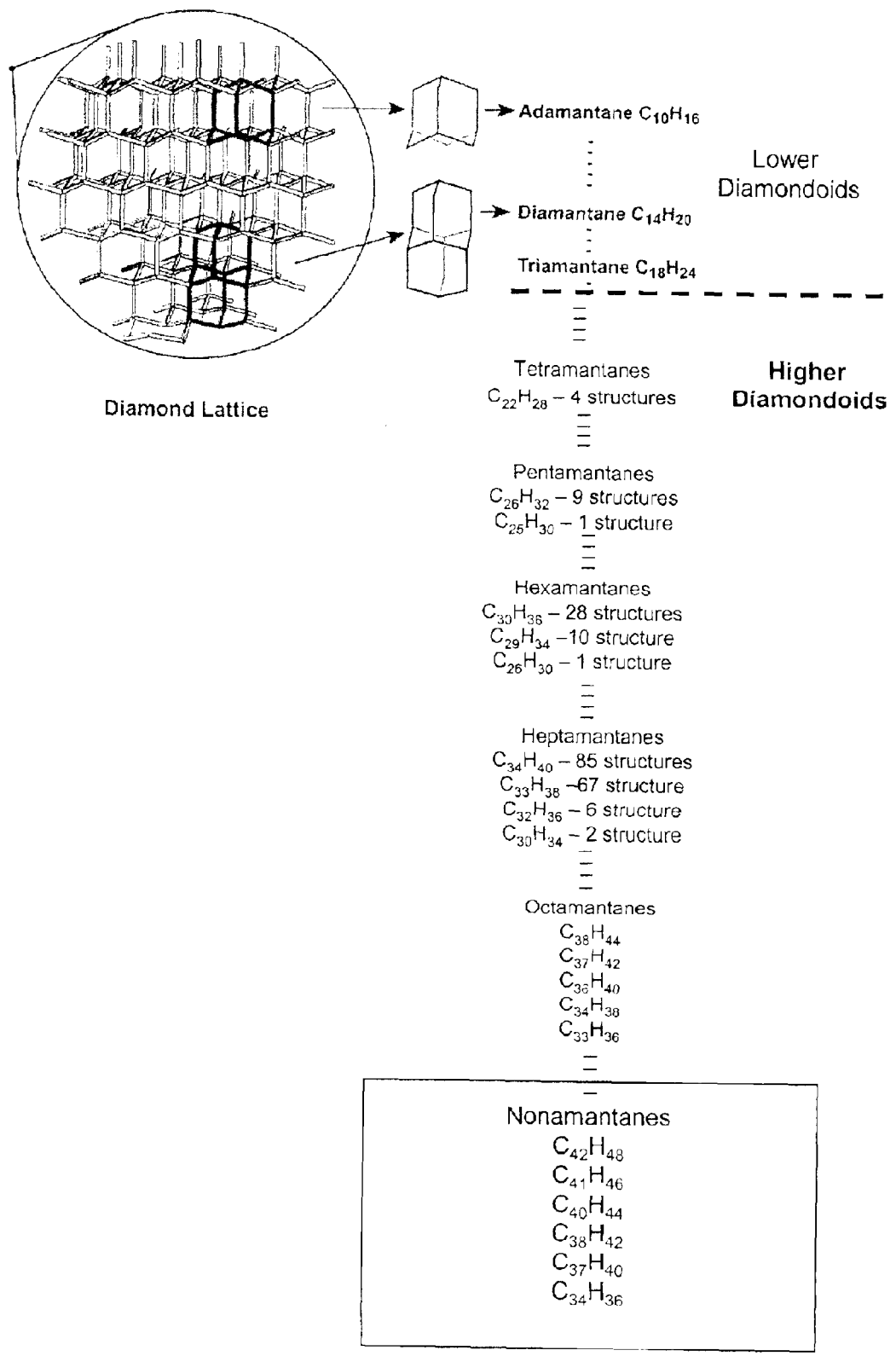
FIG. 1 illustrates the cage-shaped structure of diamondoids and their correlation to diamonds. Specifically.
Figure 2:
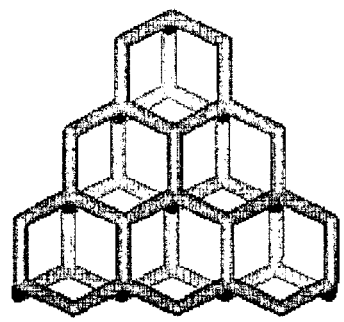
FIG. 2 illustrates the carbon framework example of a symmetrical and an enantiomeric nonamantane.
Figure 2:
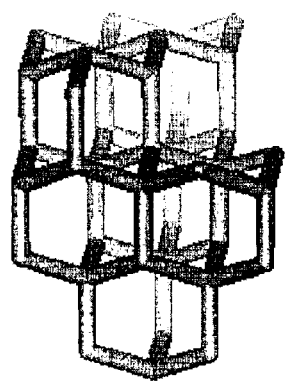
Figure 2:
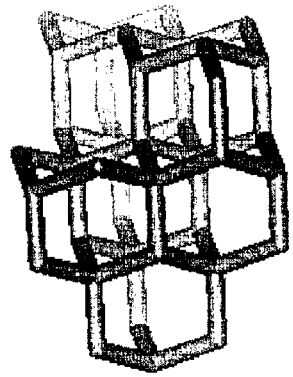

The term "diamondoids" refers to substituted and unsubstituted caged compounds of the adamantane series including adamantane, diamantane, triamantane, tetramantane, pentamantane, hexamantane, heptamantane, octamantane, nonamantane, decamantane, undecamantane, dodecamantane, and the like and also including all isomers and stereoisomers thereof. The compounds have a "diamondoid" topology, which means their carbon atom arrangement is superimposable on a fragment of the diamond lattice (FIG. 1). Substituted diamondoids comprise from 1 to 10 and preferably 1 to 4 independently-selected alkyl substituents. Diamondoids include "lower diamondoids," "nonamantanes," "higher diamondoids" and "nonnonamantane higher diamondoids" as these terms are defined herein.

The term "nonamantanes" refers to diamondoids that are the face-fused nononamers of adamantane. Among the core structures there are six families of nonamantanes having the following molecular formulas: $C_{42}H_{48}$ (molecular weight 552), $C_{41}H_{46}$ (molecular weight 538), $C_{40}H_{44}$ (molecular weight 524), $C_{38}H_{42}$ (molecular weight 498), $C_{37}H_{40}$ (molecular weight 484) and $C_{34}H_{36}$ (molecular weight 444). Each of the nonamantanes possesses a different three dimensional structure. Nonamantanes include substituted materials as described for diamondoids, generally.

The term "nonamantane component" refers to any single substituted or unsubstituted nonamantane, including optical isomers (enantiomers).

The term "lower diamondoids" or "adamantane, diamantane and triamantane components" refers to adamantane, diamantane and triamantane and any and/or all unsubstituted and substituted derivatives of adamantane, diamantane and triamantane. These lower diamondoid components show no isomers or chirality and are readily synthesized, distinguishing them from "higher diamondoids".

The term "higher diamondoids" refers to any and/or all substituted and unsubstituted tetramantane components; to any and/or all substituted and unsubstituted pentamantane components; to any and/or all substituted and unsubstituted hexamantane components; to any and/or all substituted and unsubstituted heptamantane components; to any and/or all substituted and unsubstituted octamantane components; to any and/or all substituted and unsubstituted nonamantane components; to any and/or all substituted and unsubstituted decamantane components; to any and/or all substituted and unsubstituted undecamantane components; as well as mixtures of the above as well as isomers and stereoisomers of tetramantane, pentamantane, hexamantane, heptamantane, octamantane, nonamantane, decamantane, and undecamantane. Those higher diamondoids which are not nonamantane components are referred to as "nonnonamantane higher diamondoids."

The term "feedstock" or "hydrocarbonaceous feedstock" refers to hydro-carbonaceous materials comprising recoverable amounts of one or more nonamantane components. Preferably, such feedstocks include gas condensates, refinery streams, and oil including oil derived from reservoir rocks, oil shale, tar sands, source rocks, and the like. Such feedstocks typically, but not necessarily, comprise lower diamondoids and other higher diamondoids as well as nondiamondoid components. The latter is typically characterized as comprising components having a boiling point both below and above nonamantane components, which show molecular weights from 444 to 552 and therefore show a range of boiling points beginning at about 470° C. (atmospheric equivalent boiling point). Typical feedstocks may also contain impurities such as sediment, metals including nickel and vanadium and other inorganics. They may also contain heteromolecules containing sulfur, nitrogen and the like. All of these materials which are not nonamantane components are referred to as "nonnonamantane materials or nonnomantane components."

The term "enriched" when used to describe the state of purity of one or more nonamantane components refers to such materials at least partially separated from nonnonamantane materials, and in the case of "enriched" individual nonamantane components, from other nonamantane components so as to be at a concentration at least 25 and preferably at least 100 times as great as the concentration exhibited in a feedstock. Preferably "enriched" nonamantane or "enriched" nonamantane components make up at least 25%, especially at least 50% (i.e., 50–100%), more preferably at least 75% and yet more preferably at least 95% or even at least 99% by weight of the overall material in which they are present or in other words exhibit a weight purity of at least 25%, 50%, 75%, 95%, or 99% of such material.

The term "remove" or "removing" refers to processes for removal of nondiamondoid components and/or lower diamondoid components from the feedstock. Such processes include, by way of example only, size separation techniques, distillation, evaporation either under normal or reduced pressure, well head separators, chromatography, chemical extraction, crystallization and the like. For example, Chen, et al.[8] disclose distillation processes for removing adamantane, substituted adamantane, diamantane, substituted diamantane, and triamantane from a hydrocarbonaceous feedstock. Size separation techniques include membrane separations, molecular sieves, gel permeation, size exclusion chromatography and the like.

The terms "distillation" and "distilling" refer to atmospheric, reduced pressure distillation, and elevated pressure distillation conducted to concentrate nonamantane components by removal of nonnonamantane components from the feedstock based on boiling points. Unless otherwise specified, distillation temperatures are reported as atmospheric equivalents.

The terms "fractionation" and "fractionating" refer to processes in which materials in a mixture of materials are separated from each other such as by differential solubility, differential vapor pressure, differential chromatographic affinity and the like.

The terms "thermal degradation" and "pyrolytic processing" and the like refer to processes for treating a feedstock or a feedstock fraction at elevated temperature, to selectivity break down and/or pyrolyze at least a portion of nondiamondoid components in the feedstock or feedstock fraction.

The term "nondiamondoid components" refers to components of the feedstock that are not diamondoid in character wherein the term "diamondoid" is as defined herein.

The term "chromatography" refers to any of a number of well known chromatographic techniques including, by way of example only, column or gravity chromatography (either normal or reverse phase), gas chromatography, high performance liquid chromatography, and the like.

The term "alkyl" refers to straight and branched chain saturated aliphatic groups typically having from I to 20 carbon atoms, more preferably 1 to 6 atoms ("lower alkyls"), as well as cyclic saturated aliphatic groups typically having from 3 to 20 carbon atoms and preferably from 3 to 6 carbon atoms ("lower alkyls" as well). The terms "alkyl" and "lower alkyl" are exemplified by groups such as methyl, ethyl, propyl, butyl, isopropyl, isobutyl, sec-butyl, t-butyl, n-heptyl, octyl, cyclopropyl, cyclobutyl, cyclopentyl, cyclohexyl and the like.

Methodology

The enriched nonamantanes of this invention can be obtained from readily available feedstocks using the following general methods and procedures. It will be appreciated that where typical or preferred process conditions (i.e., reaction temperatures, times, solvents, pressures, etc.) are given, other process conditions can also be used unless otherwise stated. Optimum reaction conditions may vary with feedstocks, but such conditions can be determined by one skilled in the art by routine optimization procedures. Detailed descriptions of methods for processing feedstocks to obtain higher diamondoid compositions are set forth in U.S. Provisional Patent Application No. 60/262,842 filed Jan. 19, 2001; U.S. Provisional Patent Application No. 60/300,148 filed Jun. 21, 2001; U.S. Provisional Patent Application No. 60/307,063 filed Jul. 20, 2001; U.S. Provisional Patent Application No. 60/312,563 filed Aug. 15, 2001; U.S. Provisional Patent Application No. 60/317,546 filed Sep. 5, 2001, and U.S. Provisional Patent Application No. 60/323,883 filed Sep. 20, 2001 These applications are herein incorporated-by-reference in their entirety.

To obtain the nonamantane compositions described herein, a feedstock is selected such that said feedstock comprises recoverable amounts of nonamantane. Preferably, such feedstock comprises at least about 1 part per trillion of nonamantane components. It is understood, of course, that feedstocks having higher concentrations of nonamantanes facilitate recovery of these materials.

Preferred feedstocks include, for example, natural gas condensates and refinery streams having high concentrations of diamondoids. With regard to the latter, such refinery streams include hydrocarbonaceous streams recoverable from cracking processes, distillations, coking and the like. Particularly preferred feedstocks include natural gas condensates from the Norphlet Formation in the Gulf of Mexico and from the LeDuc Formation in Canada The feedstocks used to obtain the compositions of this invention typically comprise nondiamondoid components having boiling points both below and above the nonamantane components as well as lower diamondoids and non-nonamantane higher diamondoids. A sufficient amount of these contaminants is removed from the feedstocks to provide treated feedstocks from which the nonamantane components can be enriched and recovered.

The removal of nondiamondoids, lower diamondoids and nonnonamantane higher diamondoids can be carried out, by way of example only, using size separation techniques such as membranes, molecular sieves, etc., evaporation and thermal separators either under normal or reduced pressures, extractors, crystallization, chromatography, well head separators, and the like. A preferred separation method typically includes distillation of the feedstock to remove nondiamondoid components as well as nonnonamantane diamondoids having boiling points less than that of the lowest boiling point nonamantane component. Temperature profiles for distillation runs and the resulting distillation cuts can be determined on the basis of the nonamantane component of interest. Preferably, the feedstock is distilled to provide cuts above and below about 335° C., atmospheric equivalent boiling point, more preferably, above and below about 345° C. atmospheric equivalent boiling point and more preferably, above and below about 370° C. atmospheric equivalent boiling point. In each instance, the lower cuts, which are enriched in lower diamondoids and low boiling point nondiamondoid components, are discarded. Distillation can be operated to provide several cuts in the temperature range of interest to provide the initial isolation of the identified nonamantane. The cuts, which are enriched in nonamantane or a particular nonamantane component of interest, are retained and may require further purification. For recovery of nonamantanes, the preferred distillation cuts are taken at temperatures of from 380° C. to about 630° C., preferably from 425° C. to about 590° C. and most preferably 465° C. to about 550° C. (atmospheric equivalent temperature). It being understood that substituted nonamantanes may accordingly shift these preferred temperatures to higher temperatures due to the addition of substituent groups. Additional temperature refinements will allow for higher purity cuts for the nonamantane of interest. Other methods for the removal of contaminants and further purification of an enriched nonamantane fraction can additionally include the following nonlimiting examples: size separation techniques, evaporation either under normal or reduced pressure, crystallization, chromatography, well head separators, reduced pressure and the like.

The contaminant removal may also include a thermal degradation step either prior to or subsequent to distillation. Thermal degradation is an effective method to remove hydrocarbonaceous, nondiamondoid components from the feedstock. It is effected by heating the feedstock under vacuum conditions or in an inert atmosphere, at a temperature of at least about 390° C. or 400° C. (preferably about 410° C. to about 475° C., most preferably about 410° C. to about 450° C. for from 5 to 30 hours). The specific conditions employed are selected such that recoverable amounts of nonamantane components are retained in the feedstock. The selection of such conditions is well within the skill of the art. Preferably, thermal degradation is continued for a sufficient period of time and at a sufficiently high enough temperature to thermally degrade at least about 10% by weight of the nondiamondoids components of the feed material prior to thermal degradation. More preferably at least 50% and even more preferably at least 90% of the nondiamondoids are thermally degraded.

Thermal degradation, while a preferred embodiment, is not always necessary to facilitate the recovery, isolation or purification of the nonamantane components. Other separation methods may allow for the concentration of these nonamantane components to be sufficiently high in certain feedstocks that direct purification methods such as chromatography including preparative gas chromatography and high performance liquid chromatography and crystallization may be used to isolate nonamantane components.

Even after distillation or thermal degradation/distillation, further purification of the nonamantane components may be desired to provide the compositions of this invention. One may use purification techniques such as chromatography, crystallization, thermal diffusion techniques, zone refining, progressive recrystallization, size separation and the like. For instance, the treated feedstock can be subjected to one or more of the following additional procedures: 1) gravity column chromatography using silver nitrate impregnated silica gel; 2) multicolumn preparative capillary gas chromatography; 3) single column high performance liquid chromatography; 4) high performance liquid chromatography with multiple columns of differing selectivity; and 5) crystallization to provide crystals of the highly concentrated nonamantanes. These provisions can be combined. For example, preparative capillary gas chromatography can be coupled with high performance liquid chromatography as a first or subsequent separation method.

Further processing using these methods allow for more refined separations which can lead to a pure nonamantane component. Enantioselective (chiral) stationary phases have been applied in chromatographic methods to effectuate further separations. High performance liquid chromatography methods also offer the possibility of using chiral solvents or additives to achieve resolution of enantiomers.

For example, separation of enantiomeric forms of the nonamantanes can be achieved using several approaches. One such approach is spontaneous crystallization with resolution and mechanical separation. This approach to enantiomer resolution can be enhanced by preparation of derivatives or by the use of additives, chiral solvents, or various types of seed crystals.

Another resolution option is chemical separation under kinetic or thermodynamic control. Other suitable processes for enantiomers resolution include chiral separations, which can be preformed using a gas chromatographic (GC) see "Chiral Chromatography". T. E. Beesley, et. al, Wiley, Johnson & Sons, January 1998, incorporated herein by reference, by high performance liquid chromatographic (HPLC) and by supercritical fluid chromatographic (SFC) techniques, see "Supercritical fluids in Chromatography and Extraction". R. M. Smith, Elsevier Science, December 1997, incorporated herein by reference.

Compositions

This invention is directed to compositions comprising one or more nonamantane components wherein said compositions comprise at least about 25 weight percent nonamantane components based on the total weight of the diamondoids in the compositions. The compositions preferably comprise from about 50 to 100 weight percent, preferably about 70 to about 100 weight percent, more preferably about 90 to 100 weight percent and even more preferably about 95 to 100 weight percent nonamantane components based on the total weight of the diamondoids in the composition.

Such nonamantane-enriched compositions are obtained through the series of unit operations described above which can be used to concentrate nonamantanes to at least 25 times and more preferably at least 100 times the levels at which they occur in readily-available feedstocks. The total weight percent of nonamantane components in the compositions is preferably at least 10% by weight based upon the total weight of the composition. In a more preferred aspect the total weight percent of nonamantane components is from 50 to 100 weight percent, more preferably 70 to 100 weight percent and even more preferably 95 or 99 to 100 weight percent based upon the total weight percent of the composition.

In other aspects, the compositions comprise an enriched individual nonamantane component such that they contain from 70 to 100 weight percent, more preferably from 90 to 100 weight percent, even more preferably from 95 to 100 weight percent and most preferably from 99 to 100 weight percent of a single nonamantane component including isolated optical isomers thereof.

In a preferred embodiment, the composition aspects of this invention are directed to the nonamantanes having the molecular formula $C_{42}H_{48}$ (molecular weight 552) with the structures and lattice planes shown in FIG's 30–31, which also name these compounds using the convention as outlined in Balaban et al.[7] In a more preferred aspect, the compositions are directed to the nonamantanes having the molecular formula $C_{38}H_{42}$ (molecular weight 498) with an example structure and lattice plane shown in FIG.'s 24–25. This invention is also directed to the nonamantanes having the molecular formula $C_{41}H_{46}$ (molecular weight 538), molecular formula $C_{40}H_{44}$ (molecular weight 524), molecular formula $C_{37}H_{40}$ (molecular weight 484) and molecular formula $C_{34}H_{36}$ (molecular weight 444) with an example structure and lattice planes shown generally in FIG.'s 20–29. This invention is also directed to mixtures of the above nonamantane components as well mixtures of molecular weights of the above. In one preferred embodiment, this invention is directed to the mixture of the molecular weight 552 and molecular weight 498. The composition aspects of this invention are directed to compositions comprising one or more of these nonamantanes and for the processes for recovering said compositions enriched with such nonamantane components.

At the high nonamantane concentrations and purities achieved by the present invention, nonamantanes components can form crystal structures. Accordingly, another aspect of this invention is directed to a nonamantane crystals, whether crystals of a single nonamantane component, co-crystals comprising crystals of at least two nonamantane components or co-crystals of nonamantane components with other higher diamondoids, such as heptamantane components.

The nonamantanes recovered and isolated in this invention include substituted nonamantane components. These naturally occurring substituted nonamantanes have similar properties to the unsubstituted nonamantane components described herein and are present in the feedstocks. Substituted nonamantanes may act as useful intermediates in various nonamantane applications or can be de-alkylated to yield the corresponding unsubstituted nonamantanes. Substituted nonamantanes contain 1 to 10 alkyl substituents, and more preferably 1 to 4 such substituents.

The most prevalent substituted nonamantanes in the feedstocks used are nonamantanes substituted with lower alkyls. The most prevalent of these are methyl and ethyl-substituted nonamantanes, including methyl, ethyl, dimethyl, and trimethyl nonamantanes.

Utility

These nonamantane-containing compositions are useful in micro- and molecular-electronics and nanotechnology applications. In particular, the rigidity, strength, stability, thermal conductivity, variety of structural forms and multiple attachment sites shown by nonamantanes makes possible accurate construction of robust, durable, precision devices with nanometer dimensions. These special structural characteristics set these compounds apart from acyclic molecules, from condensed-ring systems and even from bridged-ring counterparts. The great stability, nanometer size, variable yet rigid geometry, well defined distances for places of attachment, nonplanar bridgeheads lead to their unique features. Due to the rigidity, specialized geometry, 3-dimensional shape and nanometer size of the nonamantane components, it is expected that molecular aggregates and building blocks comprising them will enable construction and synthesis of a unprecedented array of desirable materials that will find applications in molecular electronic computing devices, reduced-size machines such as molecular robots and self- replicating manufacturing systems. Alternatively, the nonamantanes may be used as novel materials of construction with special chemical, optical, electric and thermal conductivity properties for coatings, film layering and other applications taking advantage of the diamond-like properties, etc.

In addition, nonamantane-containing compositions can also be used in a high-quality lubricant which exhibits a high Viscosity Index and a very low pour point.[4] When so employed, these lubricants comprise from about 0.1 to 10 weight percent nonamantanes.

Still further, these nonamantane-containing compositions can be used as high density fuels in the manner described by Chung, et al.[5], incorporated herein by reference.

The following examples are offered to illustrate this invention and are not to be construed in any way as limiting the scope of this invention. Unless otherwise stated, all temperatures are in degrees Celsius.

As used herein and in the Figures, the following abbreviations have the following meanings. Any abbreviation not defined below has its generally accepted meaning.
API=American Petroleum Institute
ATM EQV=atmospheric equivalent
EOR Traps=end of run traps
FID=flame ionization detector
G=grams.
GC=gas chromatography
GC/MS=gas chromatography/mass spectroscopy
HPLC=high performance liquid chromatography
HYD RDG=hydrometer reading
MIN=minute
ML=milliliters
ODS=octadecylsilane
pA=pico amps
ppb=parts per billion
RI=refractive index
SFC=super critical fluid chromatography
SIM DIS=simulated distillation
ST=start
TIC=total ion current
VLT=vapor line temperature
VOL PCT=volume percent
WT PCT=weight percent

EXAMPLES

Example 1

Isolation of Nonamantane Components

The purpose of this example is to demonstrate procedures for the isolation of nonamantane components. These procedures employed Feedstock B and a pyrolysis step, however this procedure could be facilitated using other materials, such as Feedstock A, and without the pyrolysis step. After removal of lower boiling point nonnonamantane components (including some lower diamondoids and tetramantanes from the feedstock by distillation), the nonamantane components in this example were recovered by chromatography and crystallization. The distillation preferably can be operated to provide specific cuts, thus removing both lower and higher boiling point components, leaving only components within a desired boiling point range.

Figure 3:
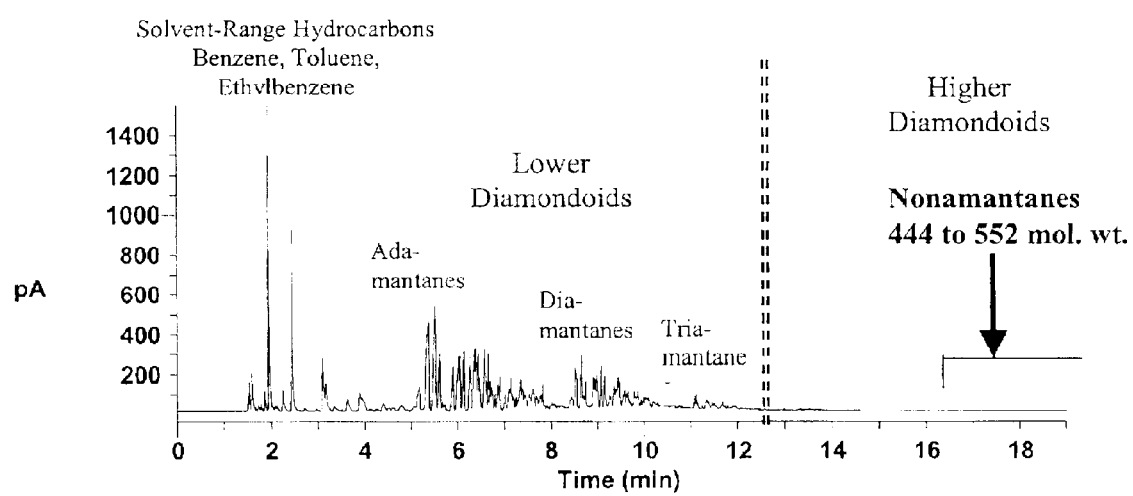
FIG. 3 illustrates the gas chromatogram of a gas condensate feedstock; one of the original feedstocks used in the Examples (Feedstock A). Nonamantanes are present at low concentrations.
Figure 4:
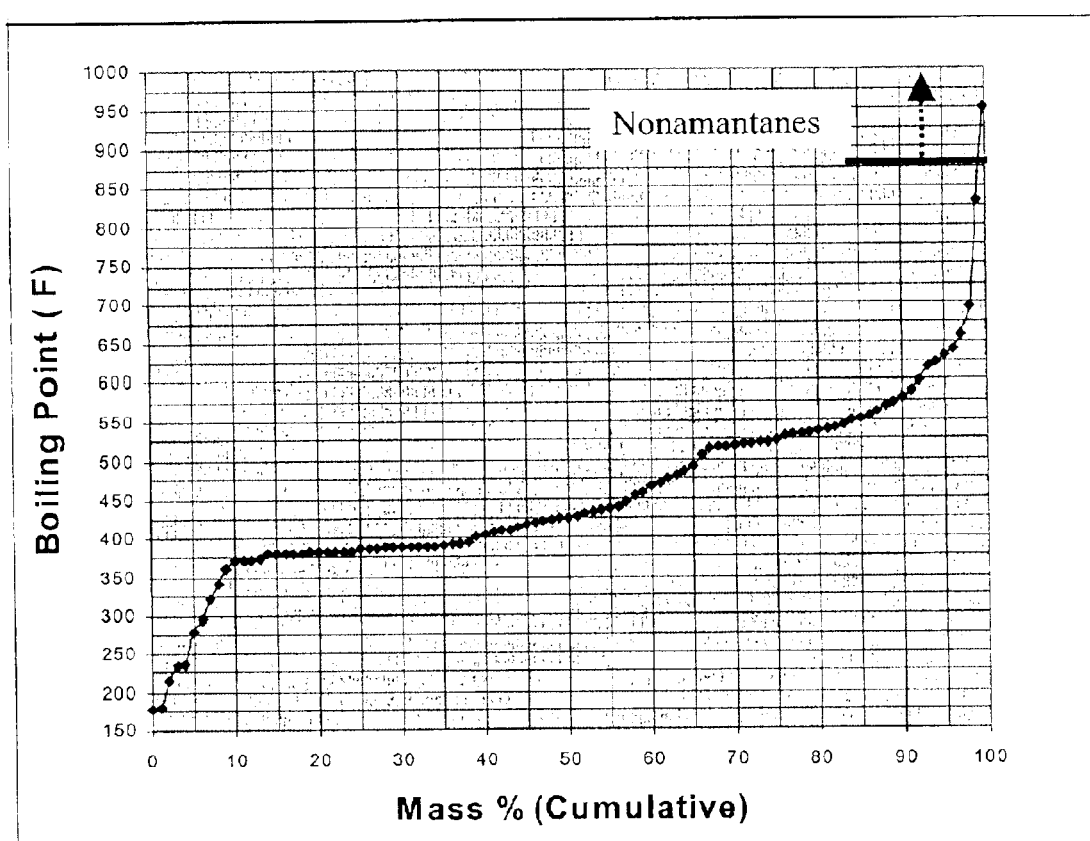
FIG. 4 illustrates a simulated distillation profile of a gas condensate feedstock containing petroleum byproducts used in the Examples (Feedstock B). Boiling points depicted are atmospheric equivalents. Nonamantanes were found in the atmospheric residue (650° F.+) of Feedstock B.

Step 1:

Suitable starting materials were obtained. These materials included a gas condensate, Feedstock A (a gas chromatogram of this material is depicted in FIG. 3), and a gas condensate containing petroleum byproducts Feed stock B (a high temperature simulated distillation profile of this type of material is depicted in FIG. 4). Although other condensates, petroleums, or refinery cuts and products could have been used, these two materials were chosen due to their high concentration of higher diamondoids (0.3 weight percent), as determined by GC and GC/MS. Both feedstocks were light colored and had API gravities between 19 and 20° API.

Step 2:

Samples from Feedstocks A and B were distilled into a number of fractions based on boiling points to separate the lower boiling point components (nondiamondoids and lower diamondoids) and to further concentrate and enrich nonamantanes in various fractions. The yields of atmospheric distillate fractions of two separate samples of Feedstock B are shown in Table 1, below and are contrasted to the simulated distillation yields calculated for that feedstock. As seen from Table 1, the simulation data are in agreement with the distillation data.

TABLE 1

Yields of Atmospheric Distillation Fractions from Two Separate Runs of Feedstock B

| Cut (° F.) | Sim Dis Est.'d Yields (Wt %) | Feedstock B (Run 2) Yields (Wt %) | Difference |
|---|---|---|---|
| To 349 | 8.0 | 7.6 | 0.4 |
| 349 to 491 | 57.0 | 57.7 | -0.7 |
| 491 to 643 | 31.0 | 30.6 | 0.4 |
| 643 and higher | 4.0 | 4.1 | -0.1 |

TABLE 1-continued

| Cut (° F.) | Sim Dis Est.'d Yields (Wt %) | Feedstock B (Run 1) Yields (Wt %) | Difference |
|---|---|---|---|
| To 477 | 63.2 | 59.3 | 3.9 |
| 477 to 515 | 4.8 | 7.3 | -2.5 |
| 515 to 649 | 28.5 | 31.2 | -2.7 |
| 649 and higher | 3.5 | 2.1 | 1.4 |

Figure 5:
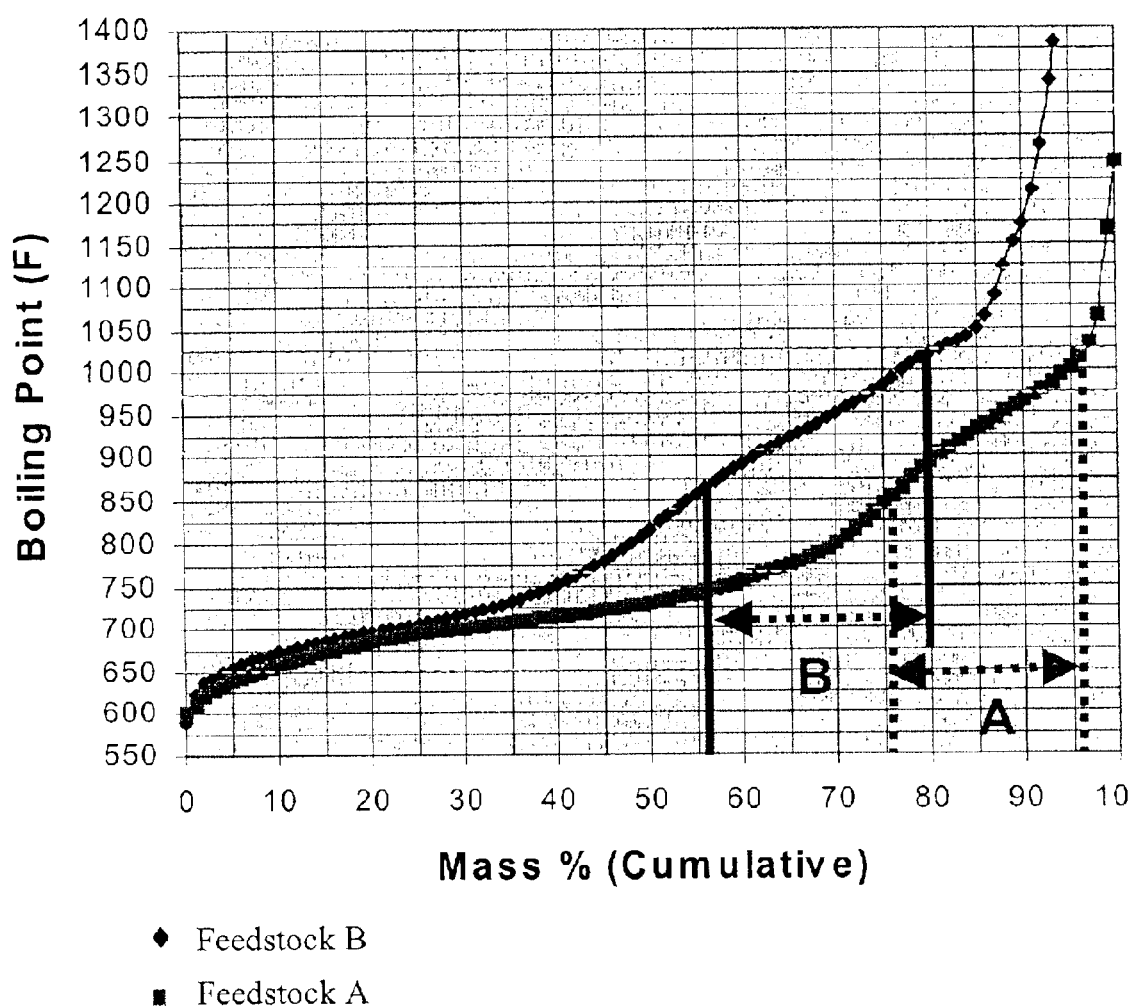
FIG. 5 illustrates a high temperature simulated distillation profile of atmospheric residue of diamondoid rich gas condensates; Feedstock A and Feedstock B. This Figure also illustrates the n-paraffin carbon number atmospheric equivalent boiling points. Labels A and B show the portions of each feedstock which contain the nonamantanes.

The higher diamondoid-containing atmospheric residue fraction from Feedstock B was in the 2 to 4 weight percent range as shown in Table 1. FIG. 5 compares a high-temperature simulated distillation profile of the atmospheric residue of the gas condensates, Feedstock A and Feedstock B. Additionally outlined is the identified location and size of the nonamantane-containing fractions. In terms of atmospheric equivalent boiling points, the nonamantane components boil predominately within the range of 380° F. to about 630° F. with a large portion within the range of 463° F. to about 549° F. Octamantanes also occur within the lower boiling point nonnomantane fractions. The lower mass percent shown for the nonamantane-containing fractions of Feedstock B, as compared to Feedstock A was due to nondiamondoid materials in Feedstock B. The nondiamondoid material can be removed by subsequent processes such as pyrolysis.

Figure 6:
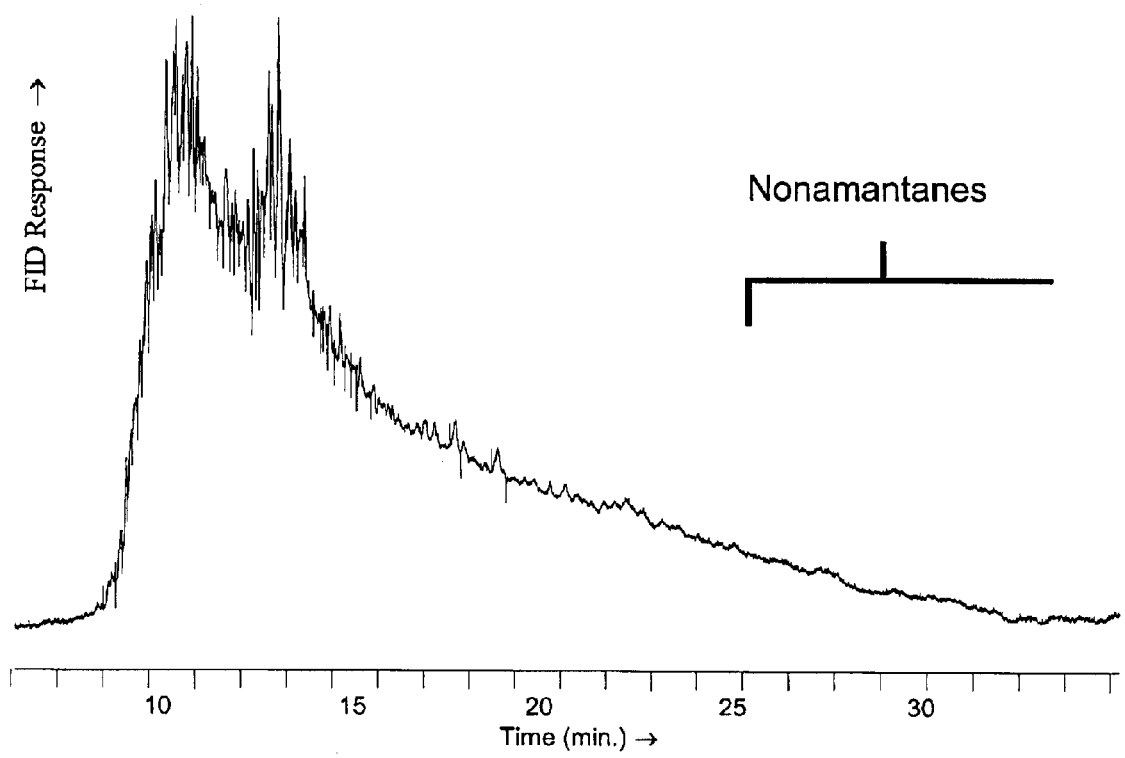
FIG. 6 illustrates gas chromatographic profiles of vacuum distillate residue containing nonamantanes and higher diamondoids from a gas condensate, Feedstock A.

A sample of gas condensate, Feedstock A was distilled into 38 fractions to remove lower diamondoids and concentrate higher diamondoids including nonamantanes as verified by GC (see FIG. 6). Fraction 38 was a recovered distillate, predominately boiling in the range of from 700 to 850° F. (atmospheric equivalent). The boiling points of these fractions are given as atmospheric equivalent temperatures, however, the actual distillation can occur at other pressures and corresponding temperatures.

Figure 7:
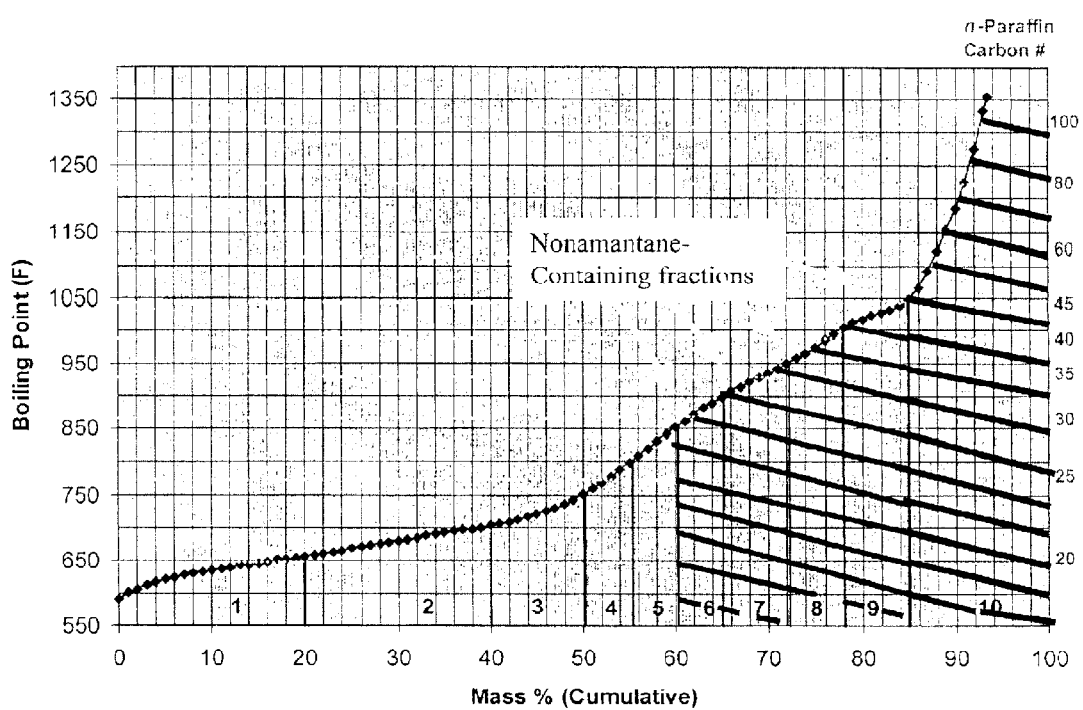
FIG. 7 illustrates a high temperature simulated distillation profile of Feedstock B using the atmospheric distillation 650° F.+ bottoms as feedstock. This FIG also illustrates the targeted cut points (1–10) for higher diamondoid isolations. Nonamantanes are contained primarily in distillate fractions 6 through 10.
Figure 8:
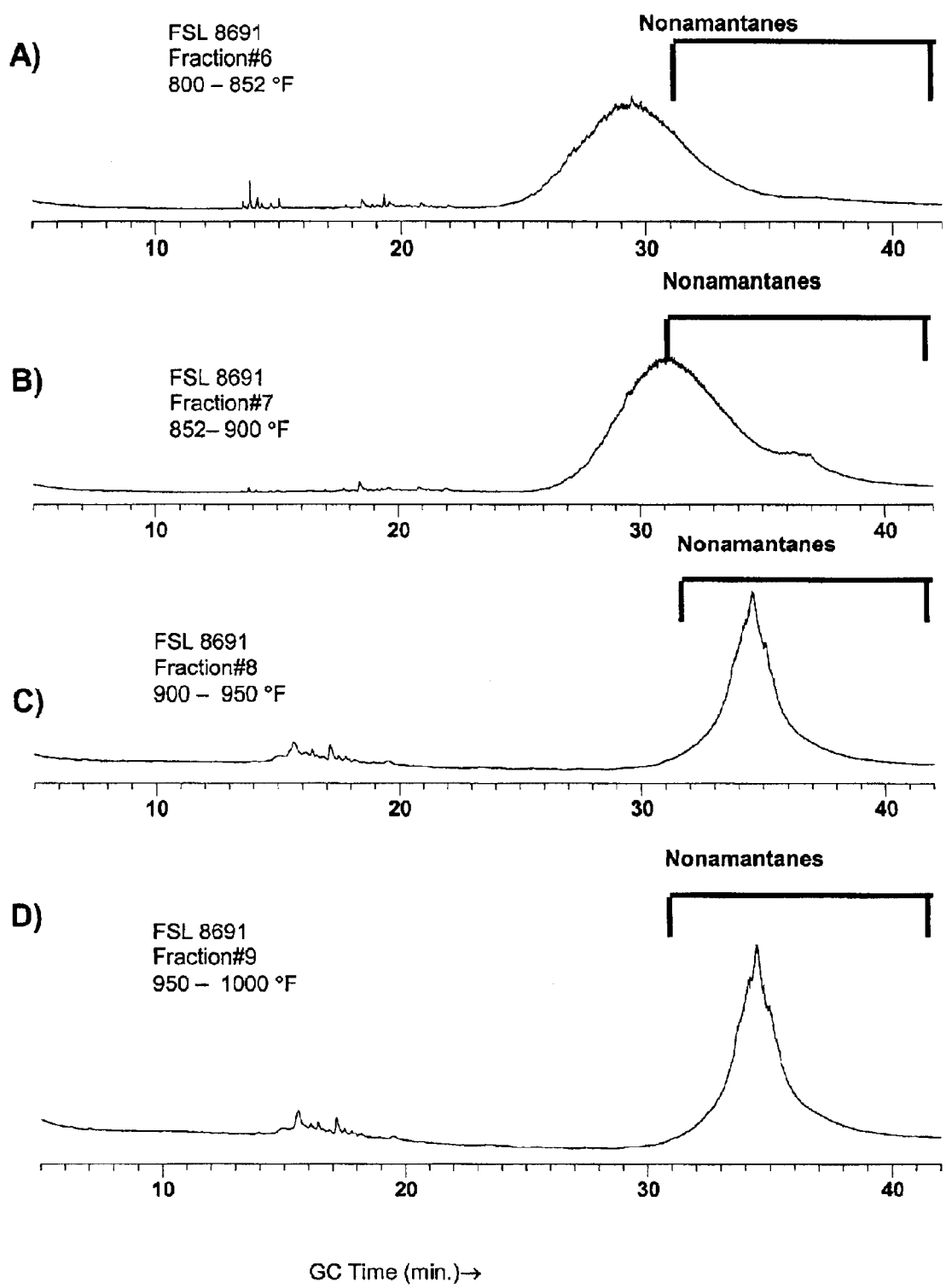
FIGS. 8 (A, B, C, D) illustrates the gas chromatograms of vacuum distillate Fractions #6, #7, #8 and #9 of Feedstock B atmospheric distillation 650° F.+ bottoms illustrated in FIG. 7.

Additionally, Feedstock B was distilled into fractions containing higher diamondoids guided by a high temperature simulated distillation curve (FIG. 7). Gas chromatograms of pertinent distillate fractions are shown in FIG. 8. Comparison of FIG's 6 and 8 shows that Feedstock B contains impurities not present in Feedstock A. The feed to the high temperature distillation process was the atmospheric 650° F.+ bottoms. Whole Feedstock B distillation reports are given in Tables 2A&B. Tables 3A&B, illustrate the distillation reports for Feedstock B 643° F.+ distillation bottoms.

TABLE 2A

Distillation Report for Feedstock B (FSL# 8471)
Feedstock B
Column Used: Clean 9" × 1.4" Protruded Packed

| | VAPOR | DISTILLATION RECORD | | | | NORMALIZED | | ACTUAL | |
|---|---|---|---|---|---|---|---|---|---|
| CUT | TEMP ° F. ST-END | WEIGHT G | VOLUME ml @ 60° F. | API 60/60 | DENSITY @ 60° F. | WT PCT | VOL PCT | WT PCT | VOL PCT |
| 1 | 226–349 | 67.0 | 80 | 38.0 | 0.8348 | 7.61 | 8.54 | 7.39 | 8.26 |
| 2 | 349–491 | 507.7 | 554 | 22.8 | 0.9170 | 57.65 | 59.12 | 55.98 | 57.23 |
| 3 | 491–643 | 269.6 | 268 | 9.1 | 1.0064 | 30.62 | 28.60 | 29.73 | 27.69 |
| COL HOLDUP | | 0.2 | 0 | 6.6 | 1.0246 | 0.02 | 0.00 | 0.02 | 0.00 |
| BTMS | 643+ | 36.1 | 35 | 6.6 | 1.0246 | 4.09 | 3.74 | 3.98 | 3.62 |
| EOR | | 0.0 | 0 | | | 0.00 | 0.00 | | 0.00 |
| TRAPS | | | | | | | | | |
| TOTALS | | 880.6 | 937 | | | 100.00 | 100.00 | 97.09 | 96.80 |
| LOSS | | 26.4 | 31 | | | | | 2.91 | 3.20 |

TABLE 2A-continued

Distillation Report for Feedstock B (FSL# 8471)
Feedstock B
Column Used: Clean 9" × 1.4" Protruded Packed

| CUT | VAPOR TEMP ° F. ST–END | WEIGHT G | VOLUME ml @ 60° F. | API 60/60 | DENSITY @ 60° F. | NORMALIZED WT PCT | NORMALIZED VOL PCT | ACTUAL WT PCT | ACTUAL VOL PCT |
|---|---|---|---|---|---|---|---|---|---|
| FEED | | 907.0 | 968 | 19.5 | 0.9371 | | | 100.00 | 100.00 |
| BACK CALCULATED API AND DENSITY | | | | 19.1 | 0.9396 | | | | |

TABLE 2B

Distillation Report for Feedstock B (FSL # 8471)
Feedstock B
Column Used: Clean 9" × 1.4" Protruded Packed

| TEMPERATURE DEGREES F. VAPOR VLT | ATM EQV. | POT | PRESSURE TORR | REFLUX RATIO | CUT NO | VOLUME ml @ 60° F. | WEIGHT G | API GRAVITIES OBSERVED HYD RDG | TEMP ° F. | 60° F. |
|---|---|---|---|---|---|---|---|---|---|---|
| 93 | 225.8 | 262 | 50.000 | 3:1 | | START OVERHEAD | | | | |
| 198 | 349.1 | 277 | 50.000 | 3:1 | 1 | 80 | 67.0 | 39.6 | 80.0 | 38.0 |
| 321 | 490.8 | 376 | 50.000 | 3:1 | 2 | 554 | 507.7 | 24.1 | 80.0 | 22.8 |
| | | | | | Cut 2 looks Milky, White crystals form in Run Down Line. Heat Lamp applied to drip tube. | | | | | |
| | | | | | Cool to transfer btms to smaller flask. | | | | | |
| 208 | 437.7 | 323 | 10.000 | 3:1 | | START OVERHEAD | | | | |
| 378 | 643.3 | 550 | 10.000 | 3:1 | 3 | 268 | 269.6 | 9.9 | 75.0 | 9.1 |
| | | | | | Shutdown due to dry pot | | | | | |
| | | | END OF RUN TRAPS | | | 0 | 0.0 | | | |
| | | | VOLUME DISTILLED | | | 902 | | | | |
| | | | COLUMN HOLDUP | | | 0 | 0.2 | 0.0 | 0.0 | 6.6 |
| | | | BOTTOMS | | | 35 | 36.1 | 7.2 | 72.0 | 6.6 |
| | | | RECOVERED | | | 937 | 880.6 | | | |
| | | | FEED CHARGED | | | 968 | 907.0 | 20.7 | 80.0 | 19.5 |
| | | | LOSS | | | 31 | 26.4 | | | |

TABLE 3A

Vacuum Distillation Report for Feedstock B (FSL # 8691)
Feedstock B - Atmospheric distillation resid 650° F. + bottoms
Column Used: Sarnia Hi Vac

| TEMPERATURE DEGREES F. VAPOR VLT | ATM EQV. | POT | PRESSURE TORR | REFLUX RATIO | CUT NO | VOL ml 60° F. | WEIGHT G | API GRAVITIES OBSERVED HYD RDG | TEMP ° F. | 60° F. |
|---|---|---|---|---|---|---|---|---|---|---|
| 315 | 601.4 | 350 | 5.000 | | | | | START OVERHEAD | | |
| 344 | 636.8 | 382 | 5.000 | | | 300 | READING | | | |
| 342 | 644.9 | 389 | 4.000 | | | 500 | READING | | | |
| 344 | 656.3 | 395 | 3.300 | | 1 | 639 | 666.4 | 7.8 | 138.0 | 4.1 |
| 353 | 680.1 | 411 | 2.500 | | | 400 | READING | | | |
| 364 | 701.6 | 430 | 2.100 | | 2 | 646 | 666.9 | 9.4 | 138.0 | 5.6 |
| 333 | 736.0 | 419 | 0.400 | | | 200 | READING | | | |
| 336 | 751.9 | 432 | 0.300 | | 3 | 330 | 334.3 | 12.4 | 139.0 | 8.3 |
| 391 | 799.9 | 468 | 0.500 | | 4 | 173 | 167.7 | 19.0 | 139.0 | 14.5 |
| 411 | 851.6 | 500 | 0.270 | | 5 | 181 | 167.3 | 26.8 | 139.0 | 21.7 |
| 460 | 899.8 | 538 | 0.360 | | 6 | 181 | 167.1 | 27.0 | 139.0 | 21.9 |
| 484 | 950.3 | 569 | 0.222 | | 7 | 257 | 238.4 | 26.2 | 139.0 | 21.2 |

TABLE 3A-continued

Vacuum Distillation Report for Feedstock B (FSL # 8691)
Feedstock B - Atmospheric distillation resid 650° F. + bottoms
Column Used: Sarnia Hi Vac

| TEMPERATURE DEGREES F. | | | | | | | API GRAVITIES | | |
|---|---|---|---|---|---|---|---|---|---|
| VAPOR | | | | | VOL | | OBSERVED | | |
| VLT | ATM EQV. | POT | PRESSURE TORR | REFLUX RATIO | CUT NO | ml 60° F. | WEIGHT G | HYD RDG | TEMP ° F. | 60° F. |
| Shut down distillation to check pot temperature limits with customer. (Drained trap material 5.3 grams) | | | | | | | | | | |
| 472 | 935.7 | 576 | 0.222 | | | | START OVERHEAD | | | |
| 521 | 976.3 | 595 | 0.340 | | 8 | 91 | 85.4 | 23.7 | 139.0 | 18.9 |
| 527 | 999.9 | 610 | 0.235 | | 9 | 85 | 80.8 | 23.0 | 139.0 | 18.2 |
| 527 | 1025.6 | 624 | 0.130 | | 10 | 98 | 93.8 | 21.6 | 139.0 | 16.9 |
| Drained remaining trap material of 16.5 grams (~4 grams of water) | | | | | | | | | | |
| | | MID AND | END OF RUN TRAPS | | | 20 | 17.8 | (mathematically combined) | | |
| | | | VOLUME DISTILLED | | | 2701 | | | | |
| | | | COLUMN HOLDUP | | | 4 | 4.0 | 0.0 | 0.0 | 3.4 |
| | | | BOTTOMS RECOVERED | | | 593 3298 | 621.8 3311.7 | 11.0 | 214.0 | 3.4 |
| | | | FEED CHARGED | | | 3298 | 3326.3 | 18.0 | 234.0 | 8.6 |
| | | | LOSS | | | −5 | 14.6 | | | |

TABLE 3B

Distillation Report for Feedstock B-btms (FSL # 8691)
Feedstock B - Atmospheric distillation resid 650° F. + bottoms
Column Used: Sarnia HiVac

| CUT | VAPOR TEMP ST–END, ° F. | WEIGHT G | VOLUME ml @ 60° F. | API 60/60 | DENSITY 60° F. | WT PCT | VOL PCT | WT PCT | VOL PCT |
|---|---|---|---|---|---|---|---|---|---|
| 1 | 601–656 | 666.4 | 639 | 4.1 | 1.0435 | 20.12 | 19.38 | 20.03 | 19.40 |
| 2 | 656–702 | 666.9 | 646 | 5.6 | 1.0321 | 20.14 | 19.59 | 20.05 | 19.62 |
| 3 | 702–752 | 334.3 | 330 | 8.3 | 1.0122 | 10.09 | 10.01 | 10.05 | 10.02 |
| 4 | 752–800 | 167.7 | 173 | 14.5 | 0.9692 | 5.06 | 5.25 | 5.04 | 5.25 |
| 5 | 800–852 | 167.3 | 181 | 21.7 | 0.9236 | 5.05 | 5.49 | 5.03 | 5.50 |
| 6 | 852–900 | 167.1 | 181 | 21.9 | 0.9224 | 5.05 | 5.49 | 5.02 | 5.50 |
| 7 | 900–950 | 238.4 | 257 | 21.2 | 0.9267 | 7.25 | 7.79 | 7.17 | 7.80 |
| 8 | 950–976 | 85.4 | 91 | 18.9 | 0.9408 | 2.58 | 2.76 | 2.57 | 2.76 |
| 9 | 976–1000 | 80.8 | 85 | 18.2 | 0.9452 | 2.44 | 2.58 | 2.43 | 2.58 |
| 10 | 1000–1026 | 93.8 | 98 | 16.9 | 0.9535 | 2.83 | 2.97 | 2.82 | 2.98 |
| COL HOLDUP | | 4.0 | 4 | 3.4 | 1.0489 | 0.12 | 0.12 | 0.12 | 0.12 |
| BTMS | 1026+ | 621.8 | 593 | 3.4 | 1.0489 | 18.78 | 17.98 | 18.69 | 18.01 |
| EOR TRAPS | | 17.8 | 20 | | | 0.54 | 0.61 | 0.54 | 0.61 |
| TOTALS | | 3311.7 | 3298 | | | 100.00 | 100.00 | 99.56 | 100.15 |
| LOSS | | 14.6 | −5 | | | | | 0.44 | −0.15 |
| FEED | | 3326.3 | 3293 | 8.6 | 1.0100 | | | 100.00 | 100.00 |
| BACK CALCULATED API & DENSITY | | | | 9.4 | 1.0039 | | | | |

TABLE 4

Elemental Composition of Feedstock B
Analyses on Feedstock B Atmospheric Distillation 650 + F Resid

| Measured | Value |
|---|---|
| Nitrogen | 0.991 wt % |
| Sulfur | 0.863 wt % |
| Nickel | 8.61 ppm |
| Vanadium | <0.2 ppm |

Table 4 illustrates data from elemental analyses of Feedstock B atmospheric distillation (650+° F.) residue including some of the identified impurities. Table 4 displays the weight percent nitrogen, sulfur, nickel and vanadium present within this feedstock. Those materials were removed in subsequent steps.

Step 3:

The higher diamondoids enriched by the separations of Step 2 were further treated to isolate a nonamantane fraction. In one case the distillation fraction 38 of Feedstock A was passed through a silica-gel gravity liquid chromatographic column (using cyclohexane elution solvent) to remove polar compounds and asphaltenes and concentrate higher diamondoids. The use of silver nitrate impregnated silica gel (10% by weight $AgNO_3$) provides cleaner diamondoid-containing fractions by removing the free aromatic and polar components. Higher diamondoids elute in the first eluting cyclohexane fraction off the column (before aromatic hydrocarbons appeared in the column eluent column. While it is not necessary to use this chromatographic separation method, it facilitates subsequent steps.

Alternatively, pyrolysis products (as disclosed in Example 2) prepared using distillate fractions of Feedstock B could be passed through a silica-gel or $AgNO_3$ impregnated silica gel gravity liquid chromatography column to remove polar compounds and asphaltenes and concentrate higher diamondoids as described above. In either instance, the distillate fractions or the pyrolysis products could be purified using this step prior to subsequent isolation procedures.

Figure 9:
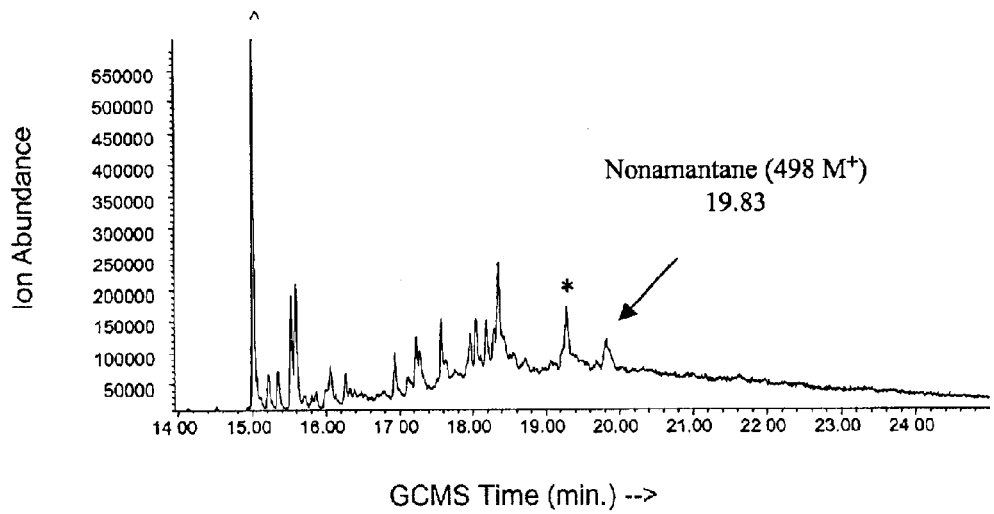
FIGS. 9 (A, B) illustrates the GC/MS total ion chromatogram and mass spectrum of nonamantane highly concentrated by high performance liquid chromatography.
Figure 9:
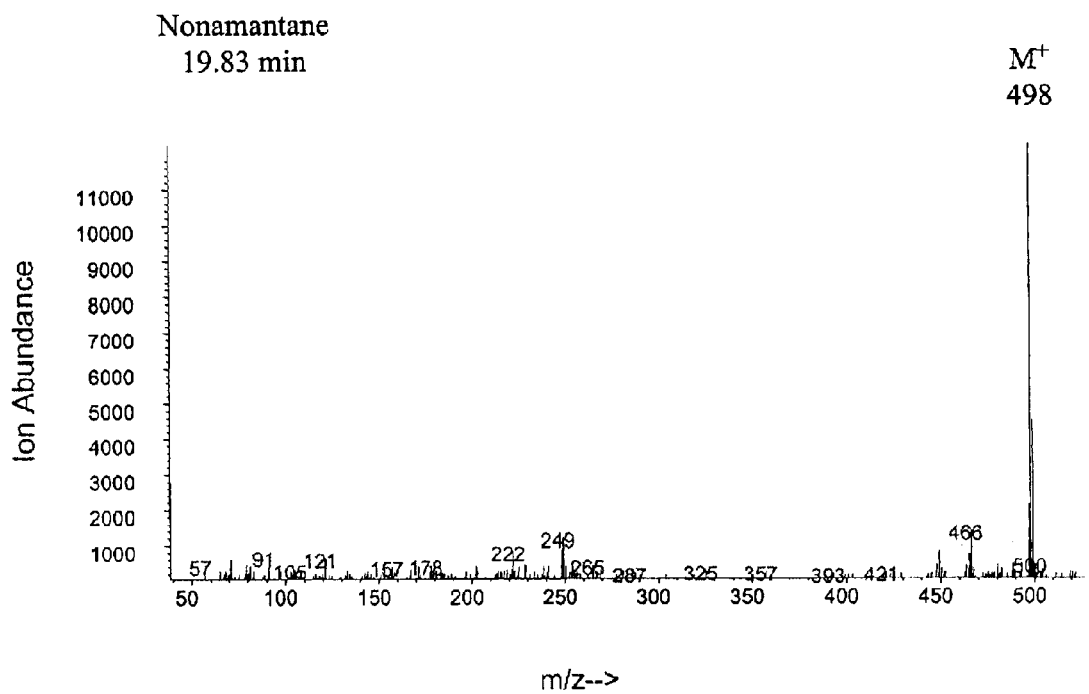

Step 4:

The nonamantane enriched fraction from step 3 was then subjected to reverse-phase HPLC, data in FIG. 9. Suitable HPLC columns for use are well known to those skilled in the art. In some cases, reverse-phase HPLC with acetone as mobile phase can be used to effect this purification. A preparative ODS HPLC run of Feedstock B distillate cut 7 pyrolysis product saturated hydrocarbon fraction was performed and the HPLC chromatogram recorded using a differential refractometer. HPLC fractions wore analyzed by GC/MS to determine nonamantane HPLC elution times (FIG. 9) and monitor purity. The HPLC columns used were two 50 cm×20 mm I. D. WHATMAN octadecyl silane (ODS) columns operated in series (Whatman columns are manufactured by Whatman Inc., USA). A 500 microliter sample of an acetone solution of the cut 7 pyrolysis product saturated hydrocarbon fraction (25 mg) was injected into the columns. The columns were set-up using acetone at 5.00 ml/min as a mobile phase carrier.

Example 2

Enrichment of Nonamantanes Using Pyrolysis.

A method was developed to further purify distillate fractions such as distillate fractions #6–9 obtained from Feedstock B—Atmospheric distillation 650° F.+ bottoms (Table 3 A/B) exploiting the great thermal stability of the nonamantanes relative to other crude oil components. FIGS. 8 (A,B,C, D) respectively, shows the GC profiles of the distillate fractions #6-9 indicating the nonnomantane portions from Feedstock B—Atmospheric distillation 650° F.+ bottoms (see FIG. 7 and Table 3A&B).

Removal of Non-diamondoids Using Pyrolysis

This method uses a reactor to pyrolyze and degrade a portion of the non-diamondoid components while enriching the diamondoids in the residue. Such reactors can operate at a variety of temperatures and pressures. FIG.'s 10(A,B) illustrates this method and shows a gas chromatogram of the Feedstock B 650° F.+ distillation fraction 7 (Table 3, FIG. 7) before pyrolysis and the resulting pyrolysis product. Pyrolysis can be used to degrade the non-diamondoid components to easily removable gas and coke like solids facilitating the isolation of nonamantanes.

A PARR® reactor, from PARR INSTRUMENT COMPANY, Moline, Ill., was used to process the distillation fractions obtained from vacuum distillation of a feedstream. For this example, Feedstock B 650° F.+ distillation fraction 7 was used as a feedstock for pyrolysis. For isolation of nonamantanes, the products of four such pyrolysis runs using from 25 to 39 grains each, of Feedstock B 650° F.+ distillation fraction 7 were combined. These pyrolysis runs were carried out at temperatures ranging from 410 to 450° C. (higher overall yields of saturated hydrocarbons were found for the lower temperature runs).

Figure 10:
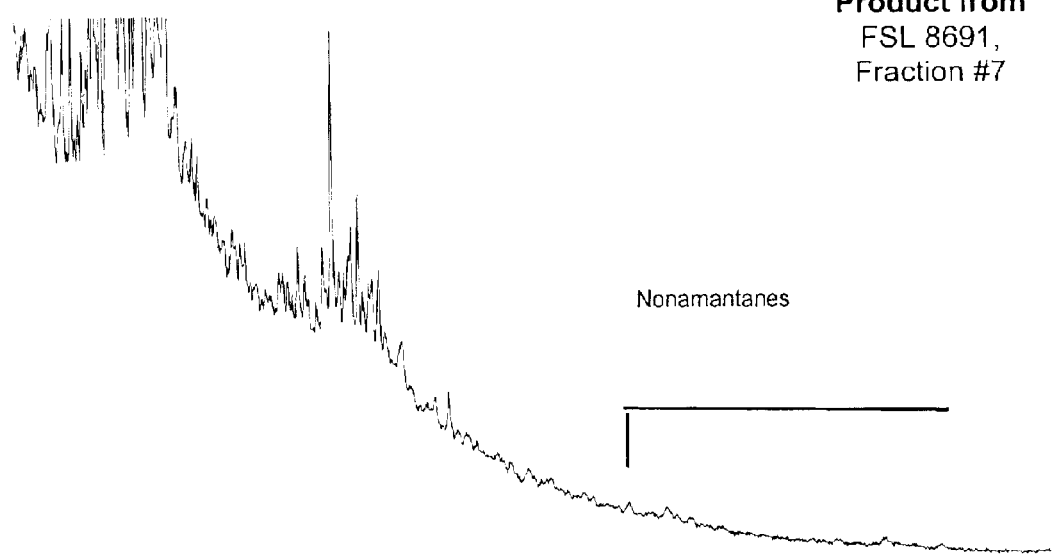
FIGS. 10 (A,B) illustrates the gas chromatograms of the concentration of nonamantanes using pyrolysis.
Figure 10:
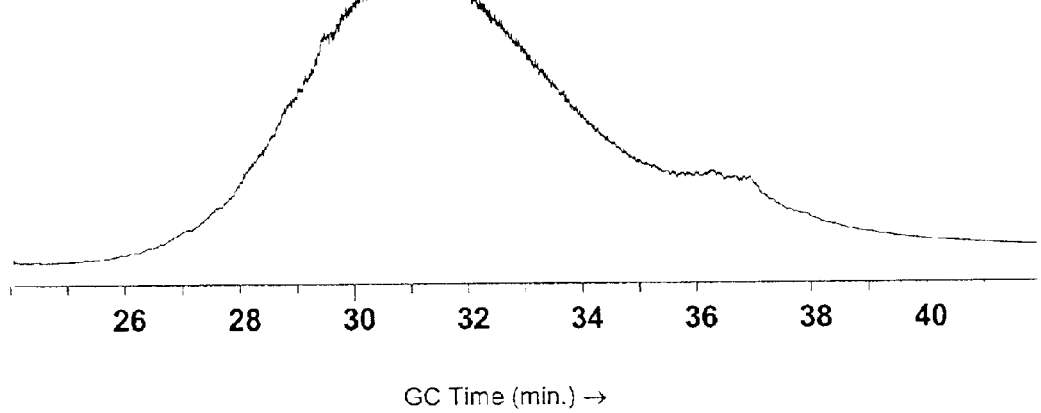

FIG. 10B shows the gas chromatogram of the distillation fraction and FIG. 10A shows the chromatograph of the products of the pyrolytic process. A comparison of the traces in FIG.'s 10(A,B) show that the pyrolysis process has removed major non-diamondoid components leaving a residue enriched in nonamantane components.

Example 3

Isolation of Nonamantanes Using HPLC and Preparative GC.

Figure 11:
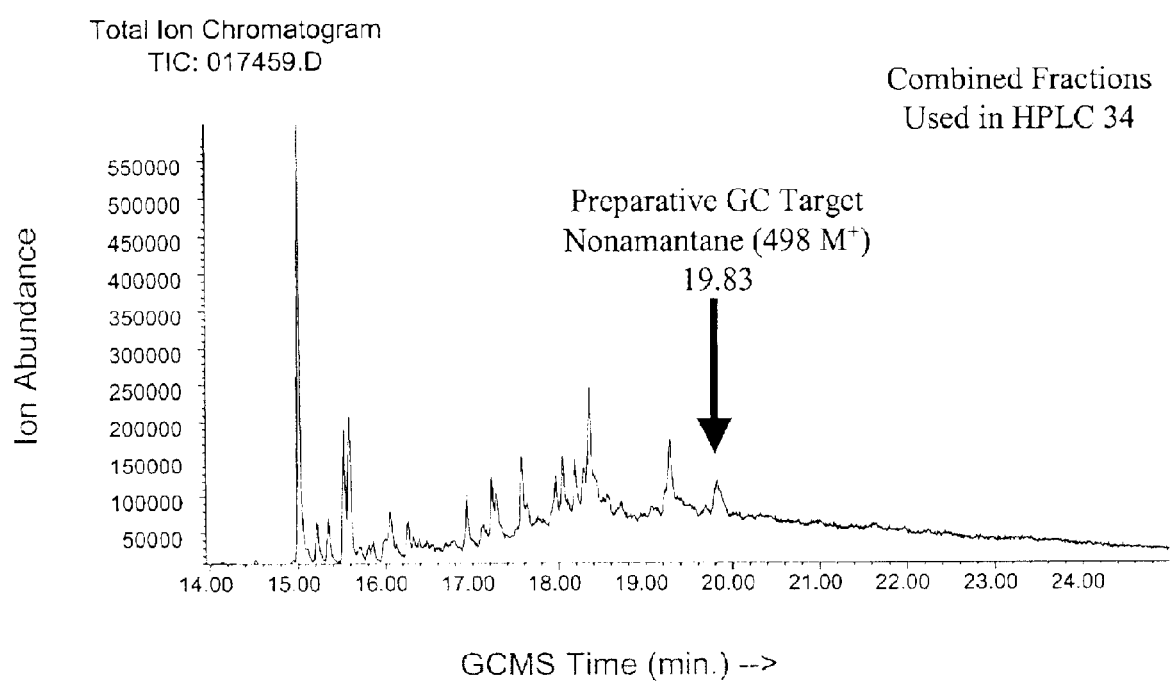
FIG. 11 illustrates results of a preparative HPLC separation of Feedstock B distillate cut #7 pyrolysis product saturated hydrocarbon fraction using octadecyl silane "ODS" columns and acetone mobile phase. This cut can be used as starting material for nonamantane isolation by preparative GC.

Ninety-five HPLC fractions from Example 1 were analyzed by GC/MS to determine the GC retention times of individual nonamantanes (an example is shown in FIG. 11). Similar assays, as above, could be prepared for the other molecular weight nonamantanes. Note that enantiomeric pairs are not resolved in this analysis.

Figure 12:
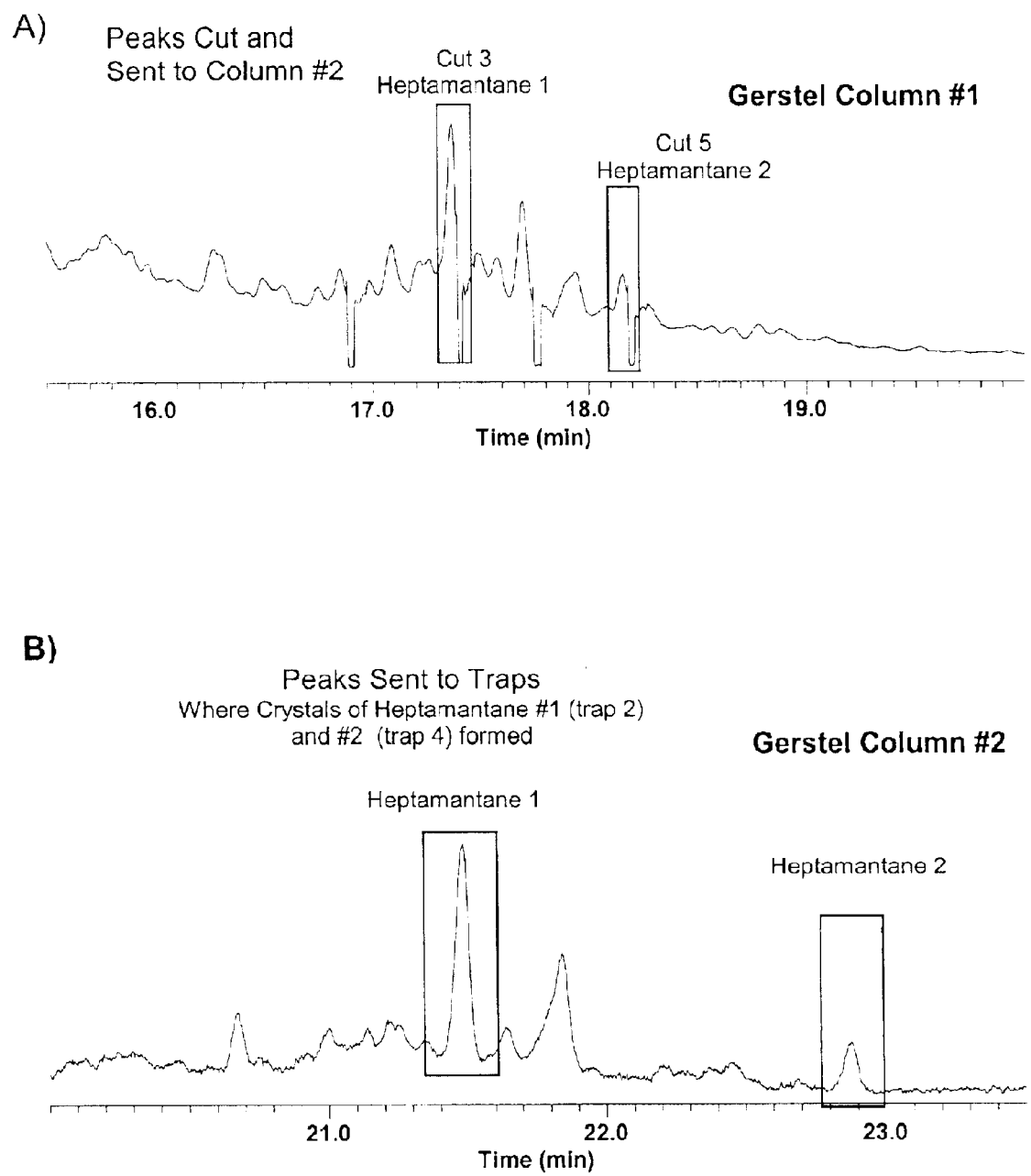
FIGS. 12 (A,B) illustrates the preparative capillary gas chromatographic data for heptamantane isolations.

Using retention times and GC patterns determined from GC/MS analysis, a two-column preparative capillary gas chromatograph can be used to isolate nonamantanes from the HPLC fractions. This methodology was demonstrated for heptamantanes as illustrated in FIG. 12. In this example the cut times for the heptamantanes were set for the first preparative capillary GC column, methyl silicone DB -1 equivalent, using the retention times and patterns from a GC/MS assay. The results are shown in the top of FIG. 12A, identified as "peaks cut and sent to column 2" which contains two of the heptamantane from Feedstock B. The preparative capillary gas chromatograph used was manufactured by Gerstel, Inc., Baltimore, Md., USA. However, other gas chromatographs could be used.

Figure 13:
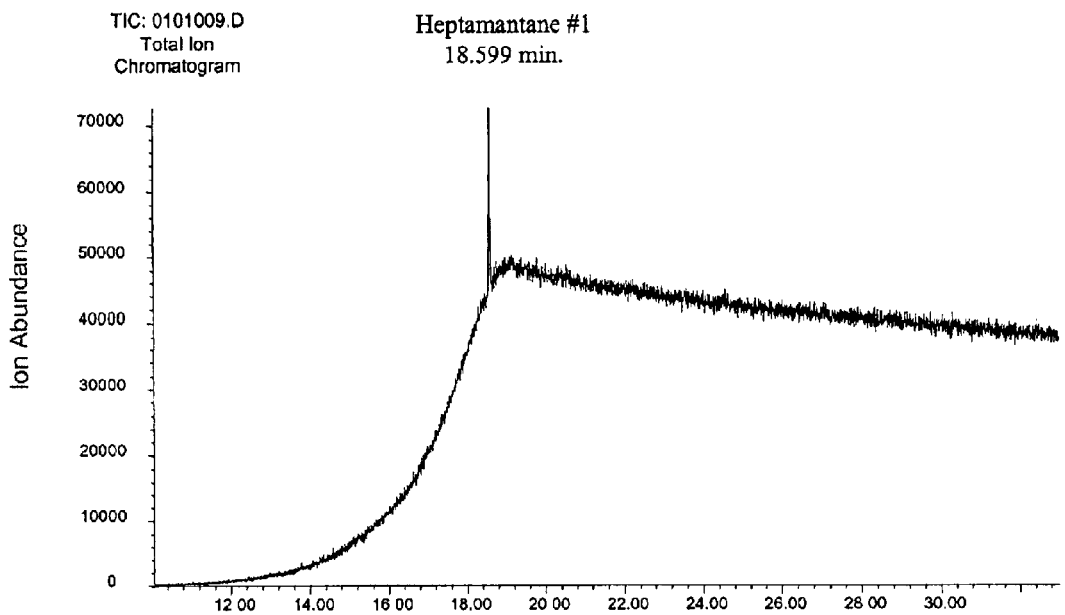
FIGS. 13 (A, B) illustrates the GC/MS total ion chromatogram and mass spectrum of heptamantane #1 isolated by preparative capillary gas chromatography.
Figure 13:
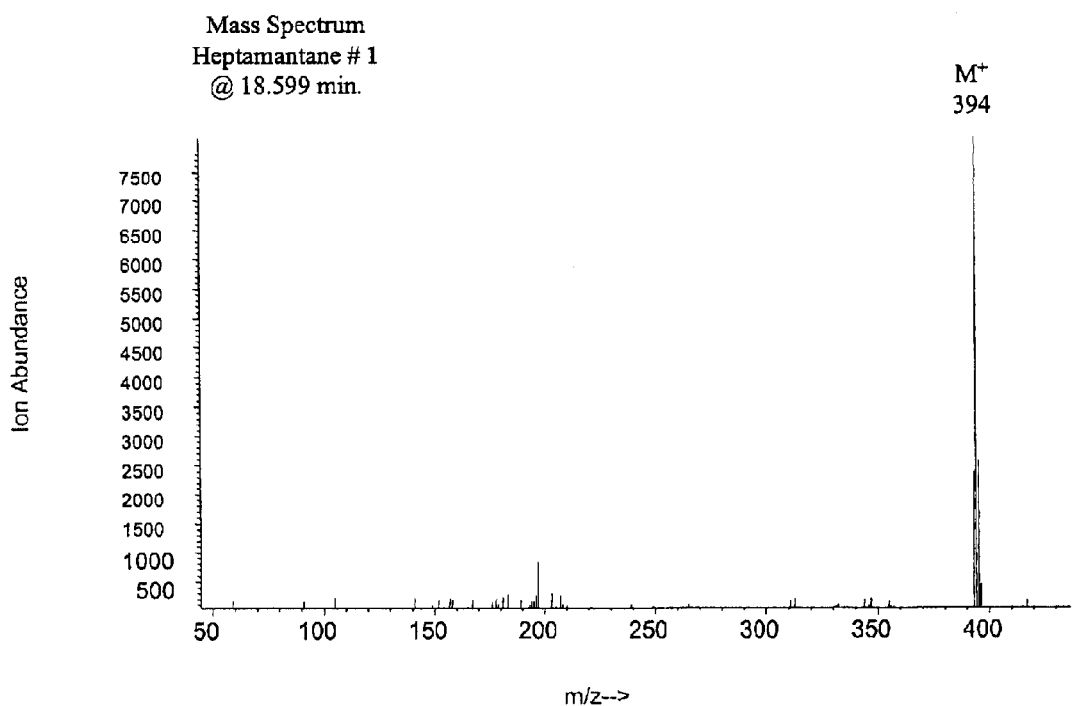
Figure 14:
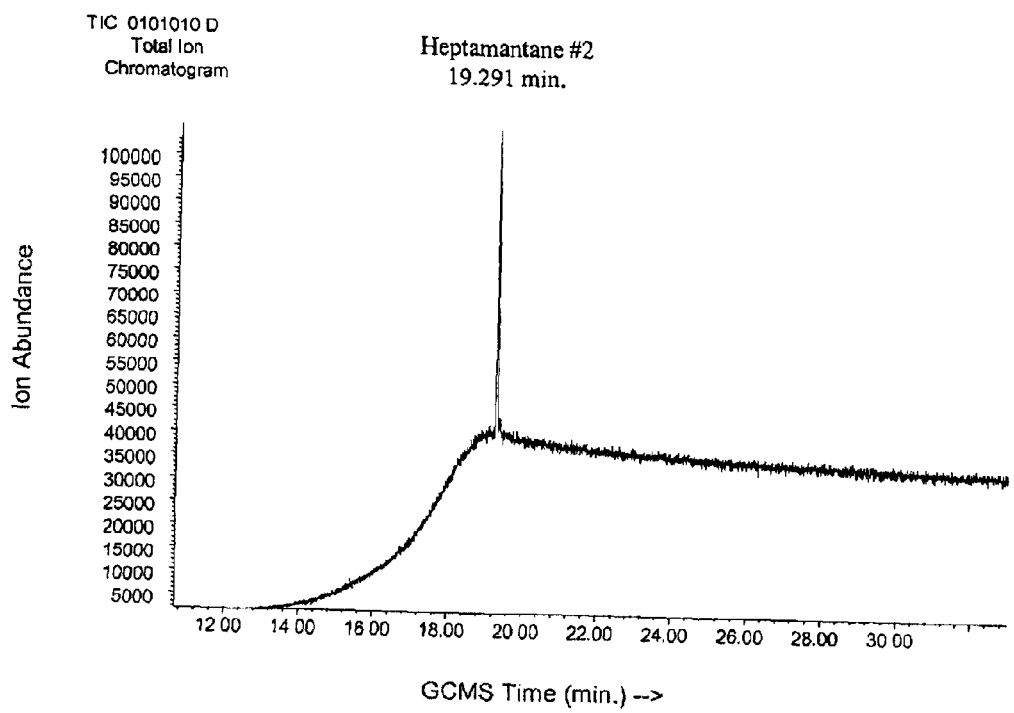
FIGS. 14 (A, B) illustrates the GC/MS total ion chromatogram and mass spectrum of heptamantane #2 isolated by preparative capillary gas chromatography.
Figure 14:
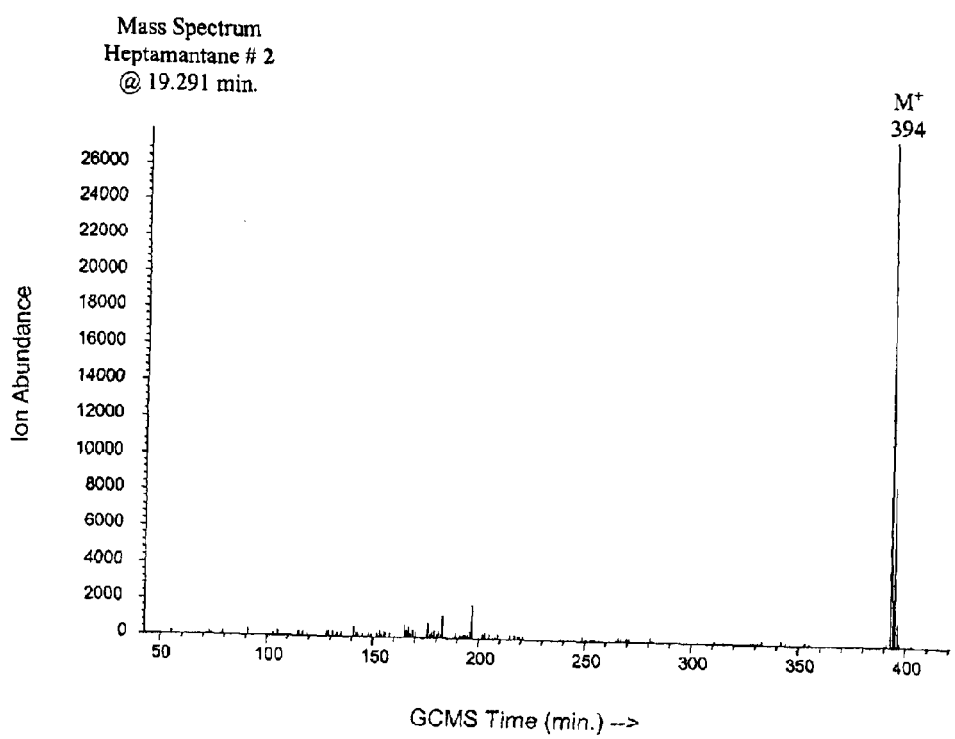

The first column was used to concentrate the heptamantanes by taking cuts that were then sent to the second column (see FIG. 12B illustrated for heptamantane #1 and #2). The second column; phenyl-methyl silicone a DB-17 equivalent, further separated and purified the heptamantanes and then was used to isolate peaks of interest and retain them into individual vials (traps 1–6). GC trap fraction 2 was collected and further processed for the separation of heptamantane #1. GC trap fraction 4 was collected and further processed for the separation of heptamantane #2. Subsequent GC/MS analysis of trap #2 material (FIG. 13) showed it to be heptamantane #1 based upon the earlier run GC/MS assay. Similarly, the GC/MS analysis of trap #4 material (FIG. 14) showed it to be heptamantane #2. This procedure can easily be used to isolate nonamantanes from HPLC fractions such those shown in FIG. 11.

Figure 15:
FIG. 15 illustrates a photomicrograph of heptamantane #1 crystals isolated from Feedstock B by preparative capillary gas chromatography.
Figure 15:
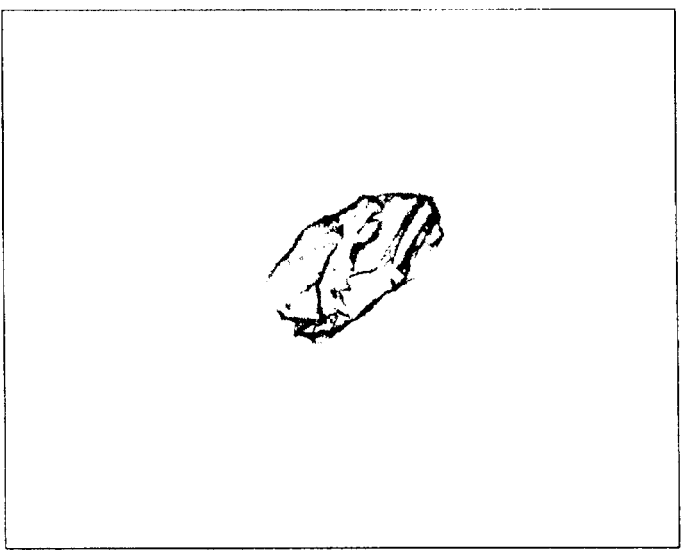
Figure 16:
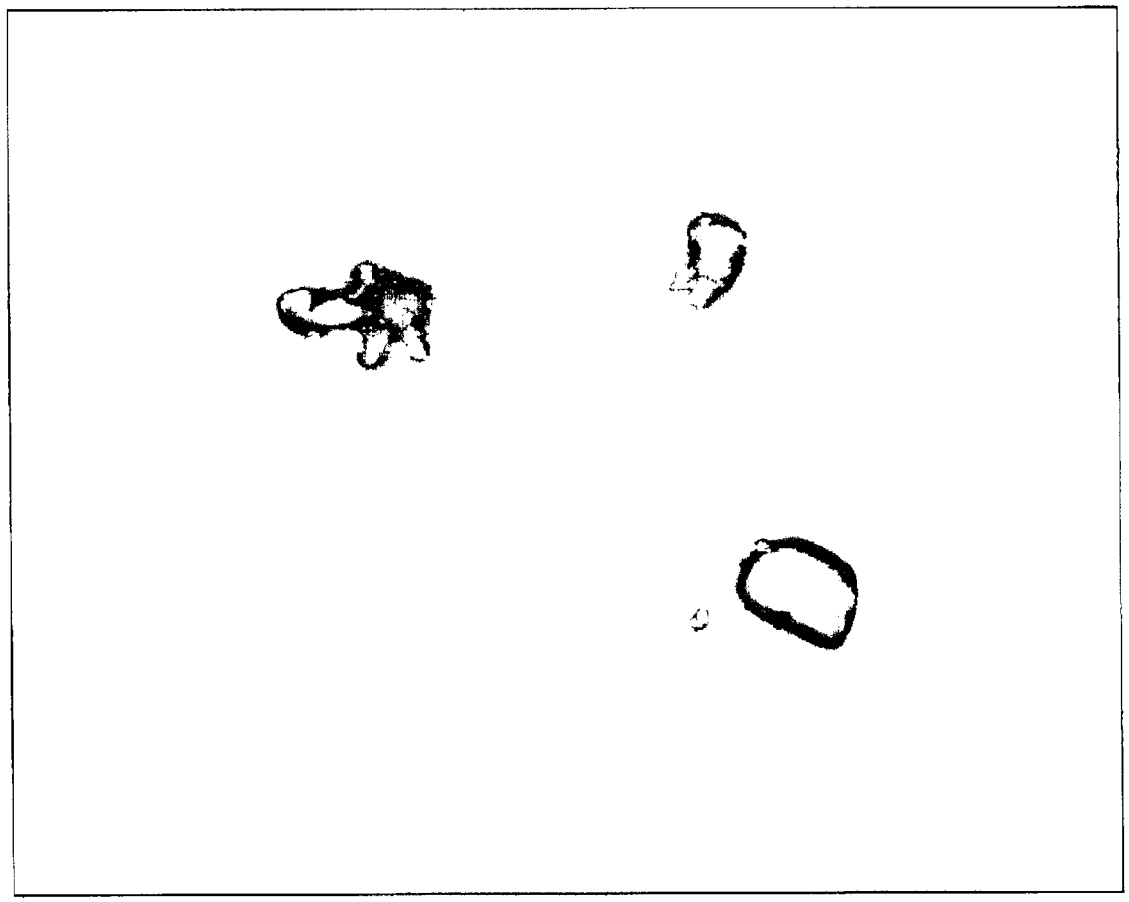
FIG. 16 illustrates a photomicrograph of heptamantane #2 crystals isolated from Feedstock B by preparative capillary gas chromatography.

The highly concentrated heptamantanes were then allowed to crystallize either directly in the trap or from solution. Under the microscope at 30×magnification, the crystals of heptamantane #1 were visible in preparative GC trap fraction 2 (see FIG. 15). These crystals were perfectly clear and showed high refractive index. Crystals of heptamantane #1 had never existed before this isolation. FIG. 16 is a photomicrograph of heptamantane #2 that crystallized in preparative GC trap 4. Crystals of heptamantane #2 had never existed before this isolation. Where concentrations are not high enough for crystallization to occur, further concentration by preparative GC may be necessary.

Example 4

Purification of Single Isomers using Dual Column Selectivity

As shown in Example 1, some nonamantanes can be enriched by using a single type of HPLC column. For isolation of nonamantane components in high purity, multiple HPLC columns can be employed. To illustrate this methodology, HPLC columns of different selectivities were used in succession to isolate single nonamantanes. The first HPLC system consisted of two Whatman M20 10/50 ODS columns operated in series using acetone as mobile phase at 5.00 mL/min. The detector used was a differential refractometer. From this HPLC run, the nonamantane containing fractions 84–88 were combined for further purification on a second HPLC system. Five such runs were completed and all nonamantane containing fractions from these runs were combined. This combined fraction contained a molecular weight 498 nonamantane and various impurities.

To purify the combined HPLC fractions 84–88 from the ODS, we injected a 50 microliter sample of approximately 1 mg of ODS HPLC combined fraction in methylene chloride onto two Hypercarb columns, two 4.6 mm I.D.×200 mm, operated in series using methylene chloride at 1.30 mL/min as mobile phase, and using a differential refractometer detector.

Figure 17:
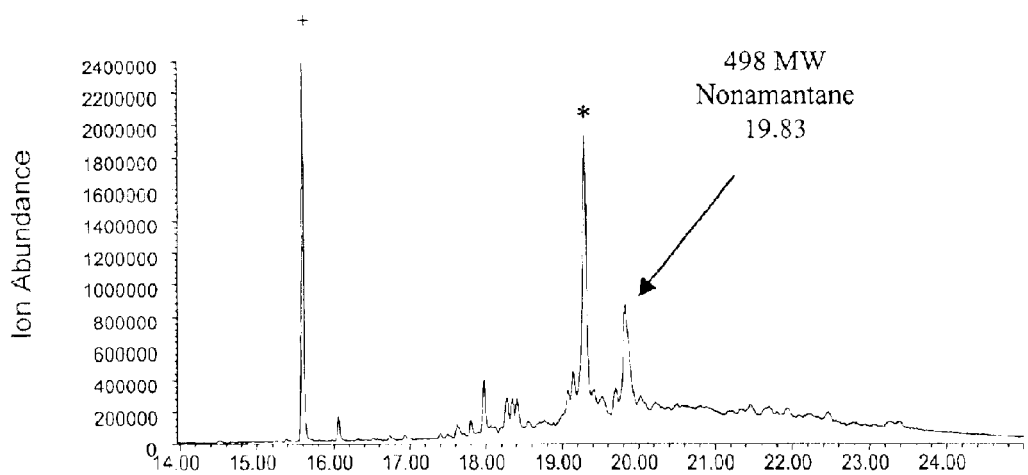
FIGS. 17 (A, B) illustrates GC/MS total ion chromatogram (TIC) and mass spectrum of a nonamantane concentrated using two different HPLC columns.
Figure 17:
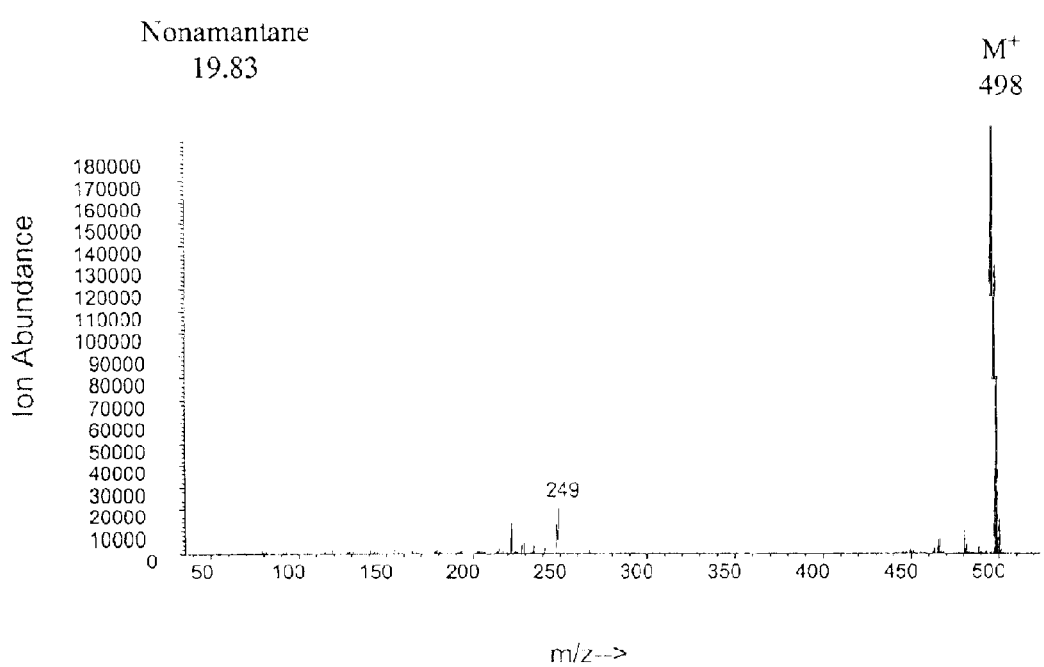
Figure 18:
FIGS. 18 (A,B) illustrates a photomicrograph of a nonamantane crystal and a mass spectra of the dissolved crystal.
Figure 18:
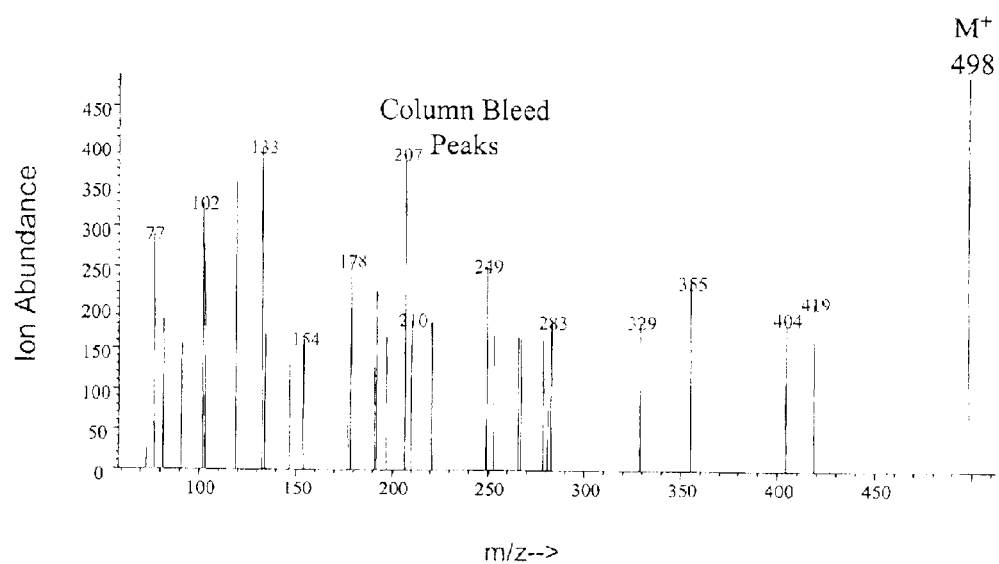

FIG. 17 shows the GC/MS total ion chromatogram (TIC) of the concentrated nonamantane containing Hypercarb HPLC fraction. The lower half of FIG. 17 illustrates the mass spectrum of the GC/MS peak. Nonamantane was isolated by a third HPLC run using the same Hypercarb stationary phase column but with a solvent consisting of methylene chloride/acetone (70:30 volume percent operating at 1.00 ml/min). The resulting isolated nonamantane crystal and mass spectrum is shown in FIG. 18.

By using a similar methodology as above, i.e. fractionating nonamantane containing ODS HPLC fractions using columns with different selectivities, such as the Hypercarb or other suitable columns, we isolated a molecular weight 498 nonamantane in high purity. This method could be repeated to isolate the nonamantanes with molecular weights of 552, and the nonamantanes of molecular weights 538, 484 and 444, which respectively are in lower abundance in our feedstocks. Note that enantiomeric nonamantanes are not resolved in GS/MS however, these enantiomers can be isolated by chiral separation methods.

FIG.'s 20 through 31 illustrate the structures with views into various diamond crystal lattice planes for one of each of the different nonamantane families. For example, FIG.'s 20–21 illustrate, molecular formula $C_{34}H_{36}$ (molecular weight 444) nonamantane structures. In a similar fashion, FIG.'s 22–23 illustrate an example ball and stick, stick with hydrogen removed, and CPK model of a molecular formula $C_{37}H_{42}$ (molecular weight 484) nonamantane; and FIG.'s 24—25 illustrate an example ball and stick, stick with hydrogen removed; and CPK model of a molecular formula $C_{38}H_{42}$ (molecular weight 498) nonamantane; and FIG.'s 26–27 illustrate an example ball and stick, stick with hydrogen removed, and CPK model of a molecular formula $C_{40}H_{44}$ (molecular weight 524) nonamantane; and FIG.'s 28–29 illustrate an example ball and stick, stick with hydrogen removed, and CPK model of a molecular formula $C_{41}H_{46}$ (molecular weight 538) nonamantane; and lastly FIG.'s 30–31 illustrate an example ball and stick, stick with hydrogen removed, and CPK model of a molecular formula $C_{42}H_{48}$ (molecular weight 552) nonamantane.

Example 5

Isolation of Substituted Nonamantanes

Substituted nonamantanes also are present in Feedstock A and B. These natural occurring substituted nonamantanes have uses similar to the unsubstituted nonamantanes and can be de-alkylated to yield the corresponding unsubstituted nonamantane. Accordingly, methods for the isolation of individual substituted nonamantanes were devised and exemplified by the isolation of alkyl substituted compounds.

Figure 19:
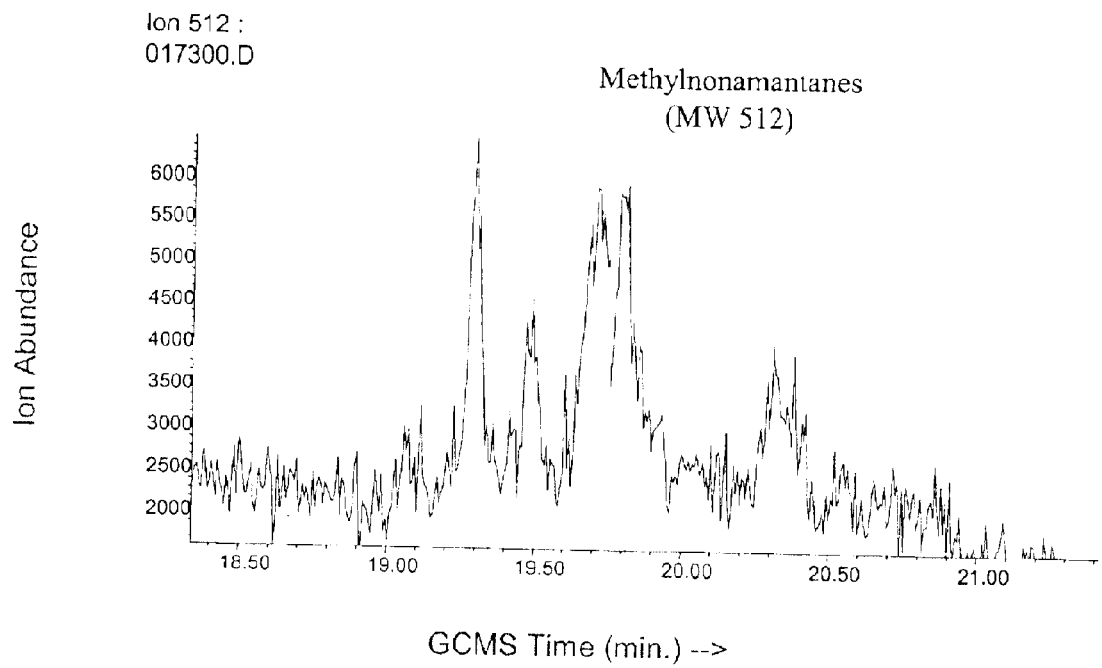
FIGS. 19 (A, B) illustrates GC/MS total ion chromatogram (TIC) and mass spectrum of a methylnonamantane (mol. wt. 512).
Figure 19:
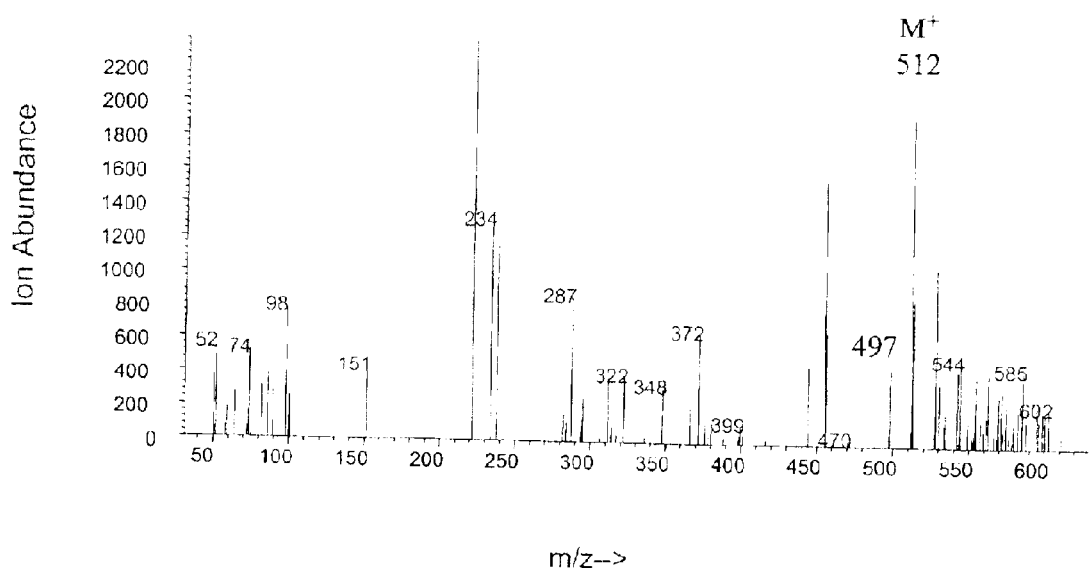
Figure 20:
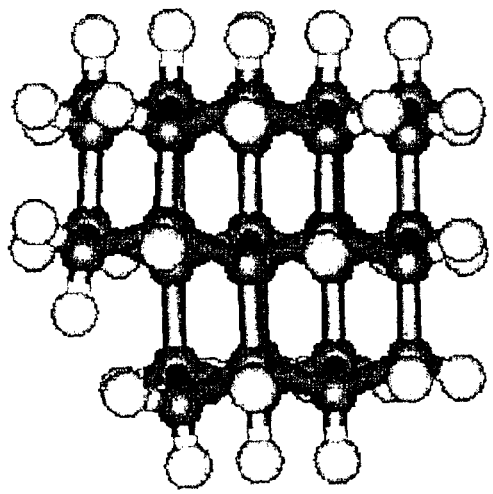
FIGS. 20–21 illustrate an example ball and stick, stick with hydrogen removed, and CPK model of a molecular formula $C_{34}H_{36}$ (molecular weight 444) nonamantane.
Figure 20:
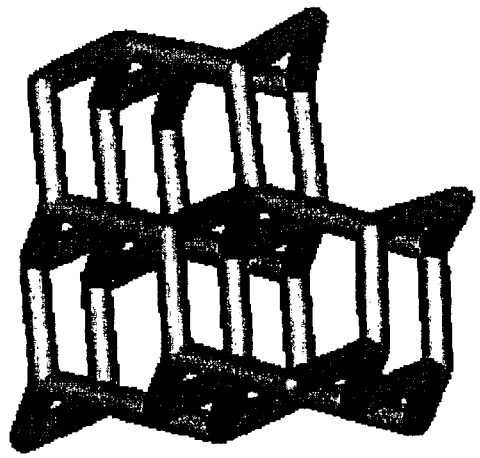
Figure 20:
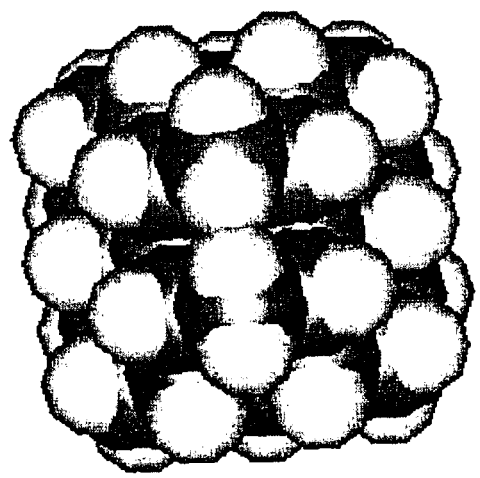
Figure 21:
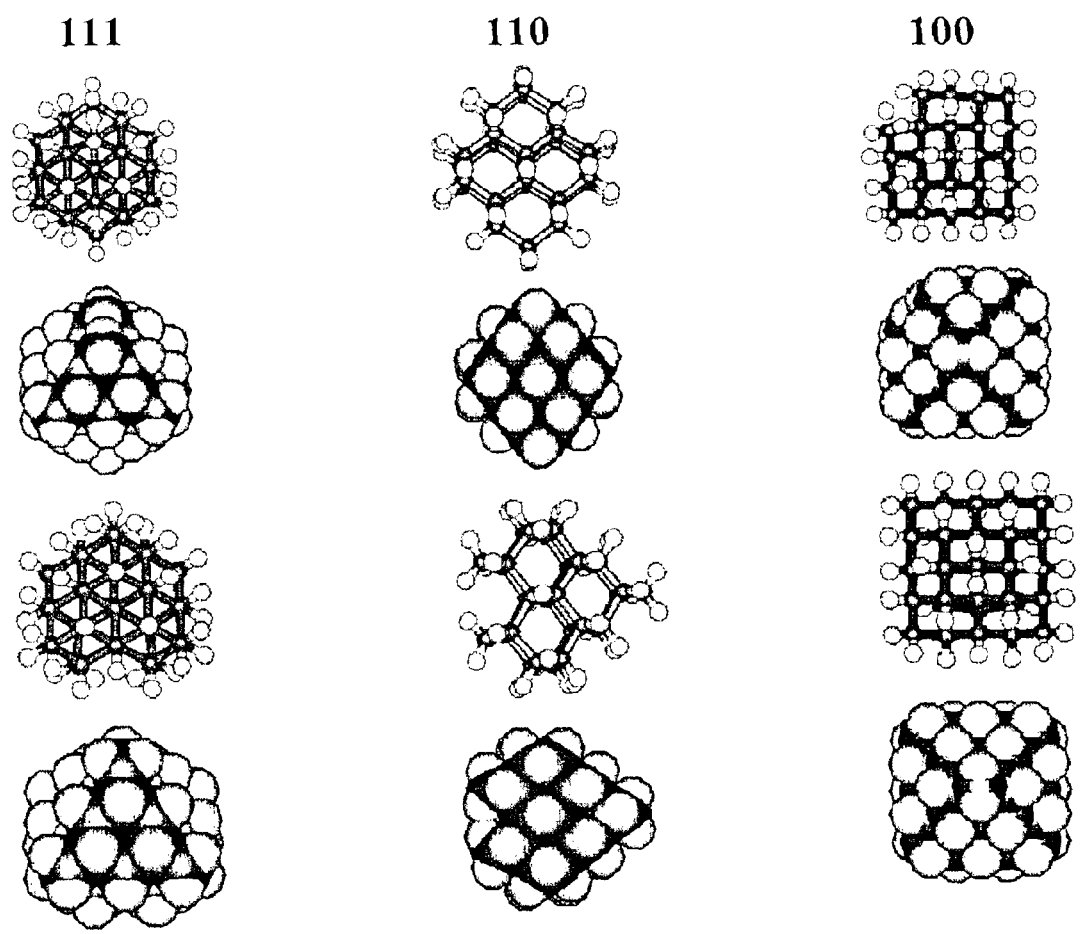
Figure 22:
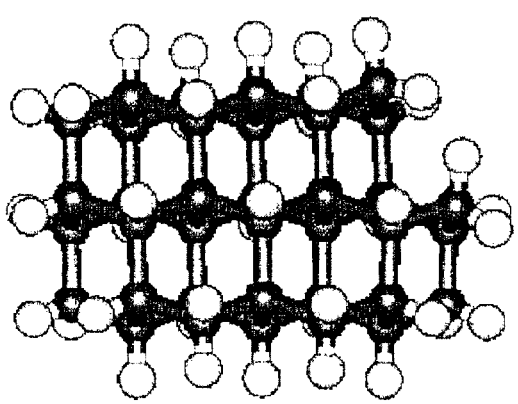
FIGS. 22–23 illustrate an example ball and stick, stick with hydrogen removed, and CPK model of a molecular formula $C_{37}H_{40}$ (molecular weight 484) nonamantane.
Figure 22:
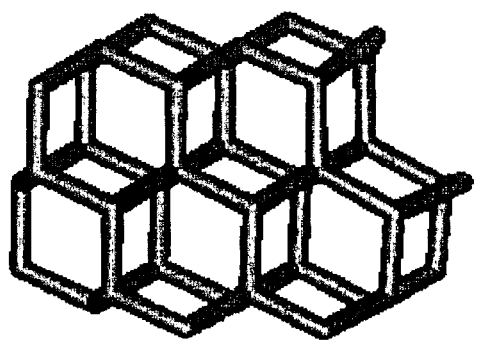
Figure 22:
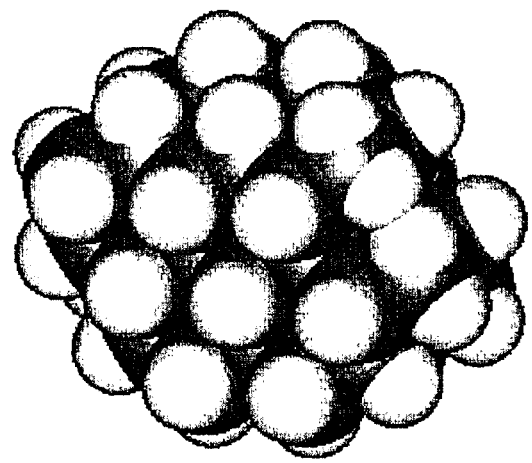
Figure 23:
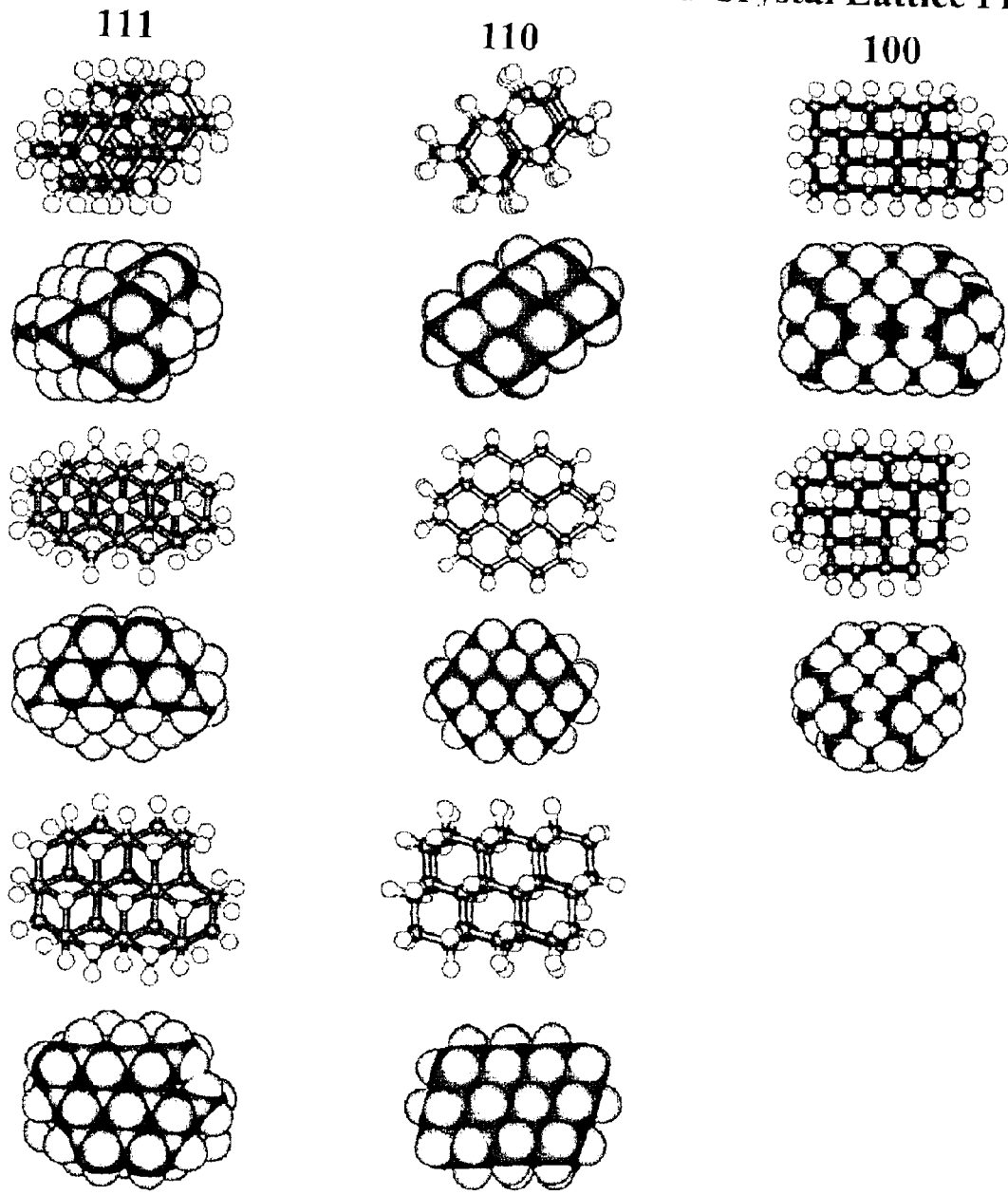
Figure 24:
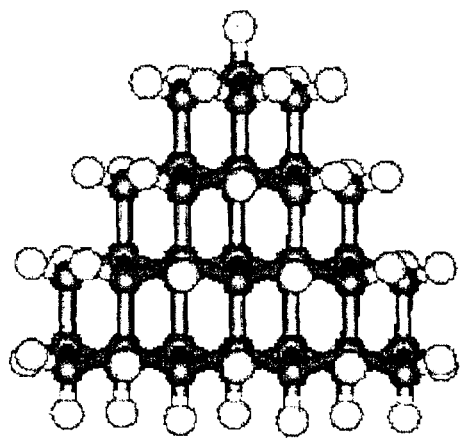
FIGS. 24–25 illustrate an example ball and stick, stick with hydrogen removed, and CPK model of a molecular formula $C_{38}H_{42}$ (molecular weight 498) nonamantane.
Figure 24:
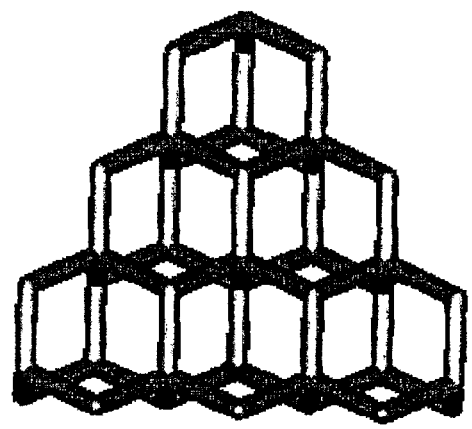
Figure 24:
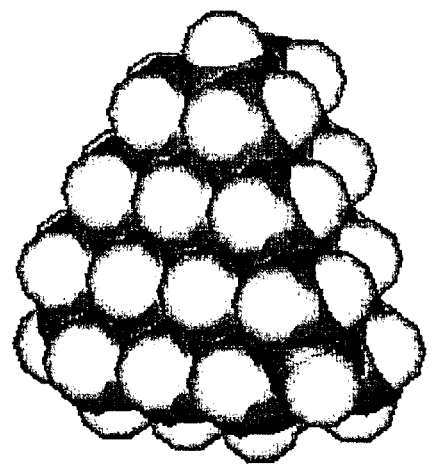
Figure 25:
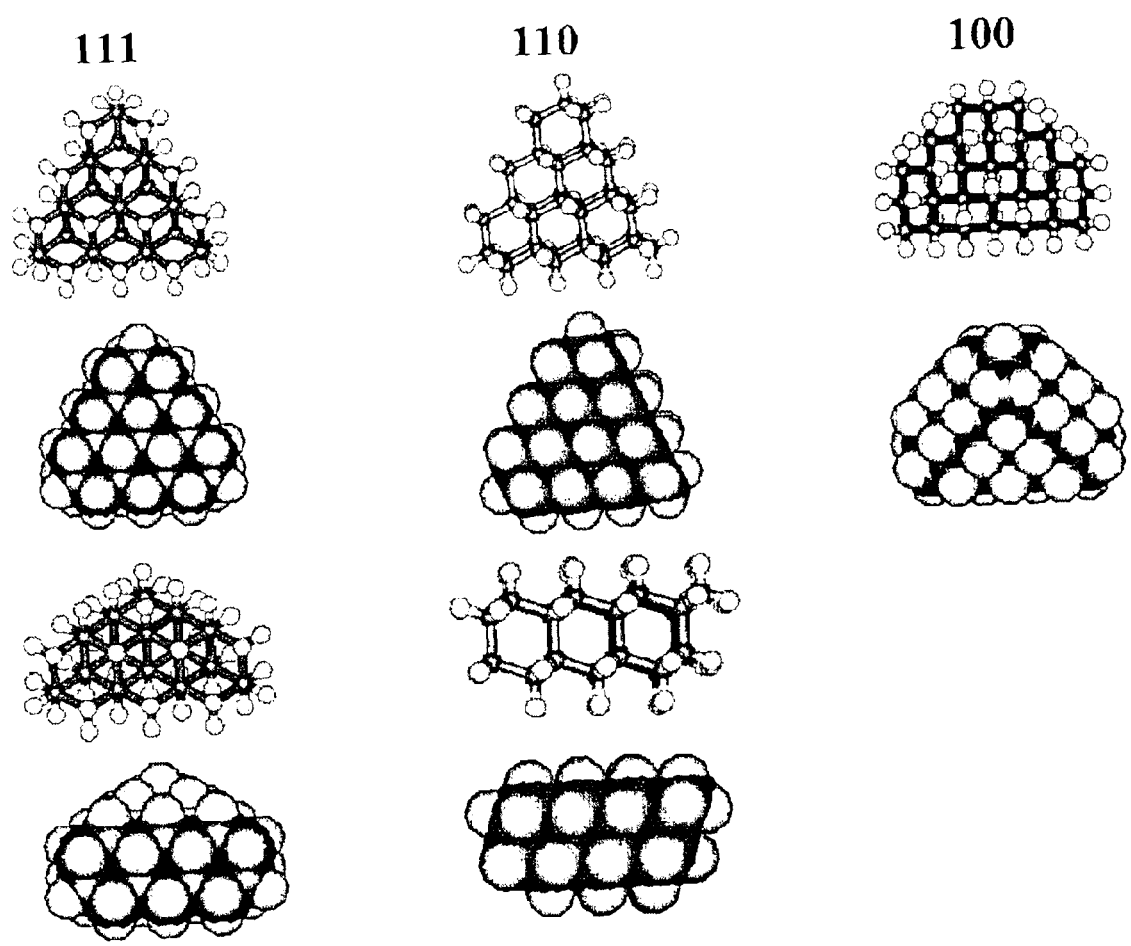
Figure 26:
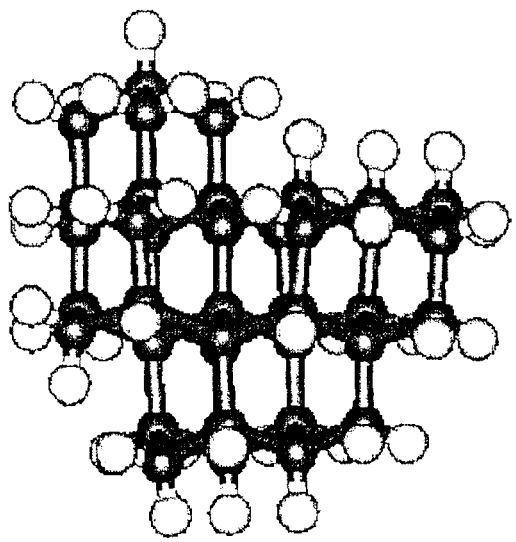
FIGS. 26–27 illustrate an example ball and stick, stick with hydrogen removed, and CPK model of a molecular formula $C_{40}H_{44}$ (molecular weight 524) nonamantane.
Figure 26:
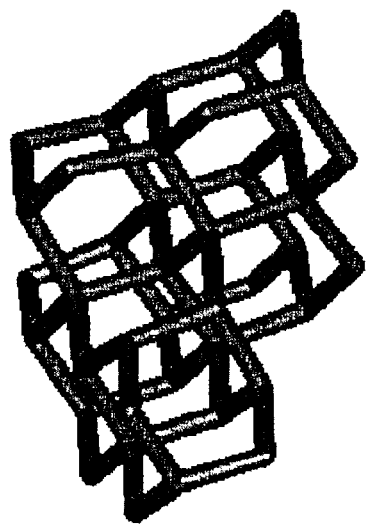
Figure 26:
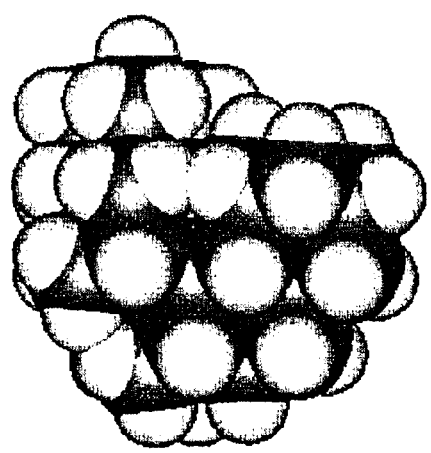
Figure 27:
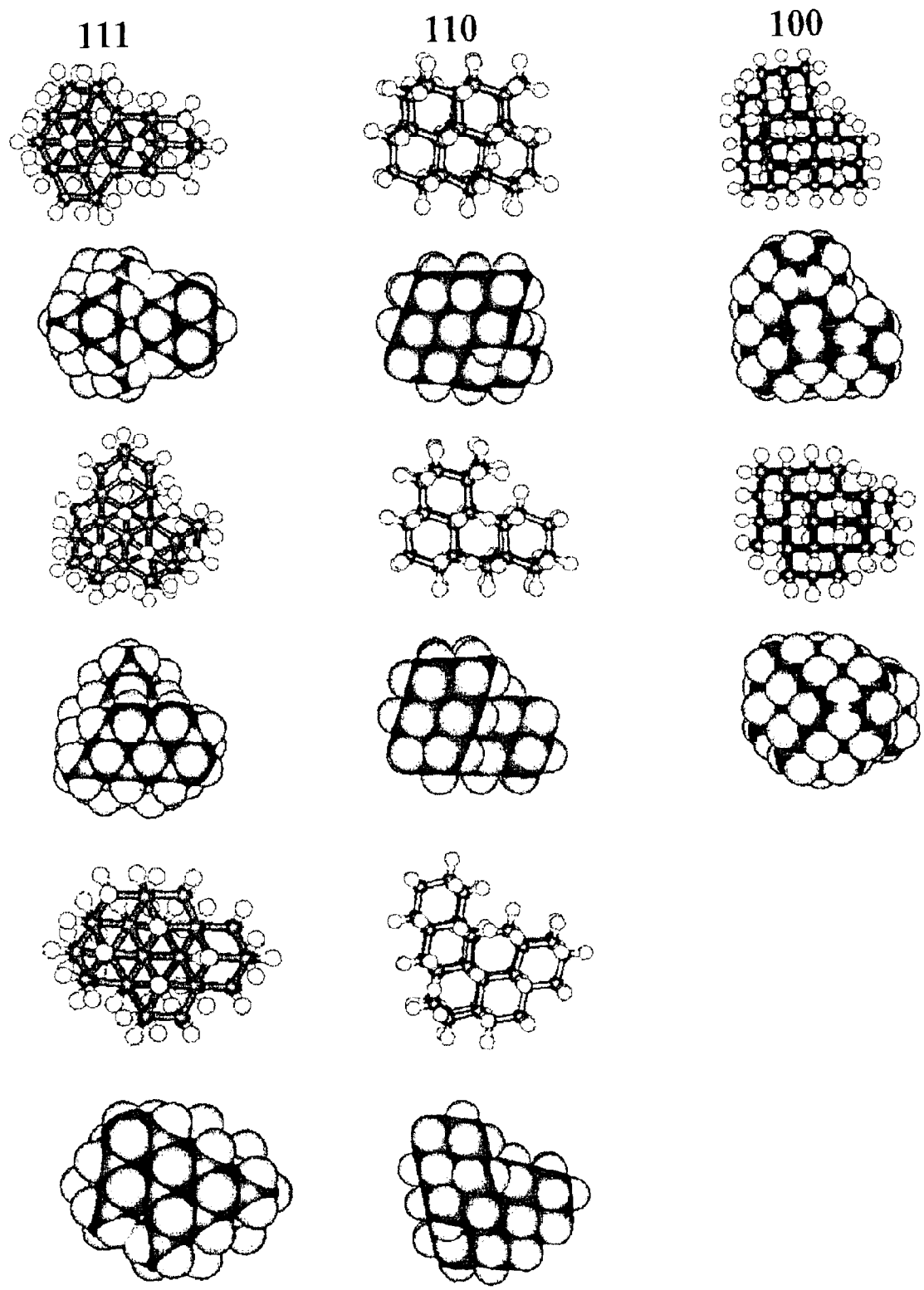
Figure 28:
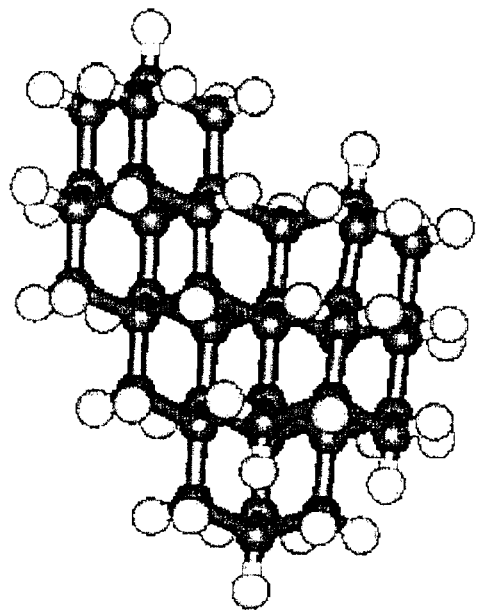
FIGS. 28–29 illustrate an example ball and stick, stick with hydrogen removed, and CPK model of a molecular formula $C_{41}H_{46}$ (molecular weight 538) nonamantane.
Figure 28:
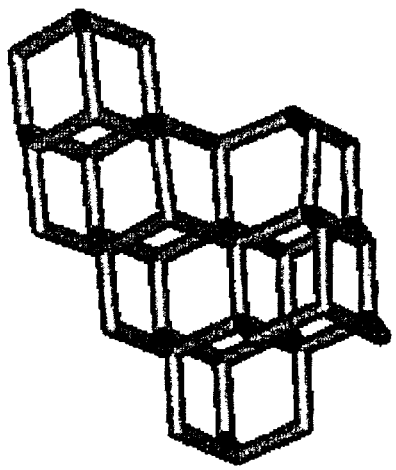
Figure 28:
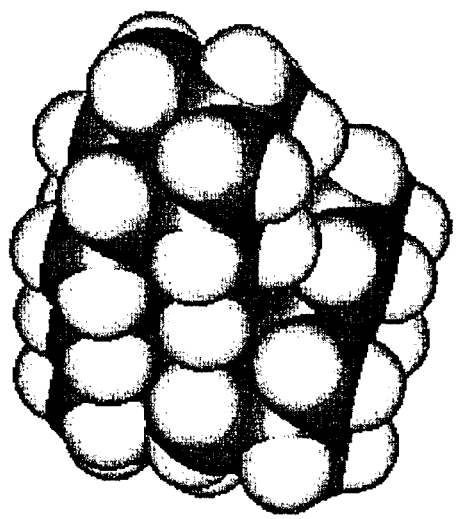
Figure 29:
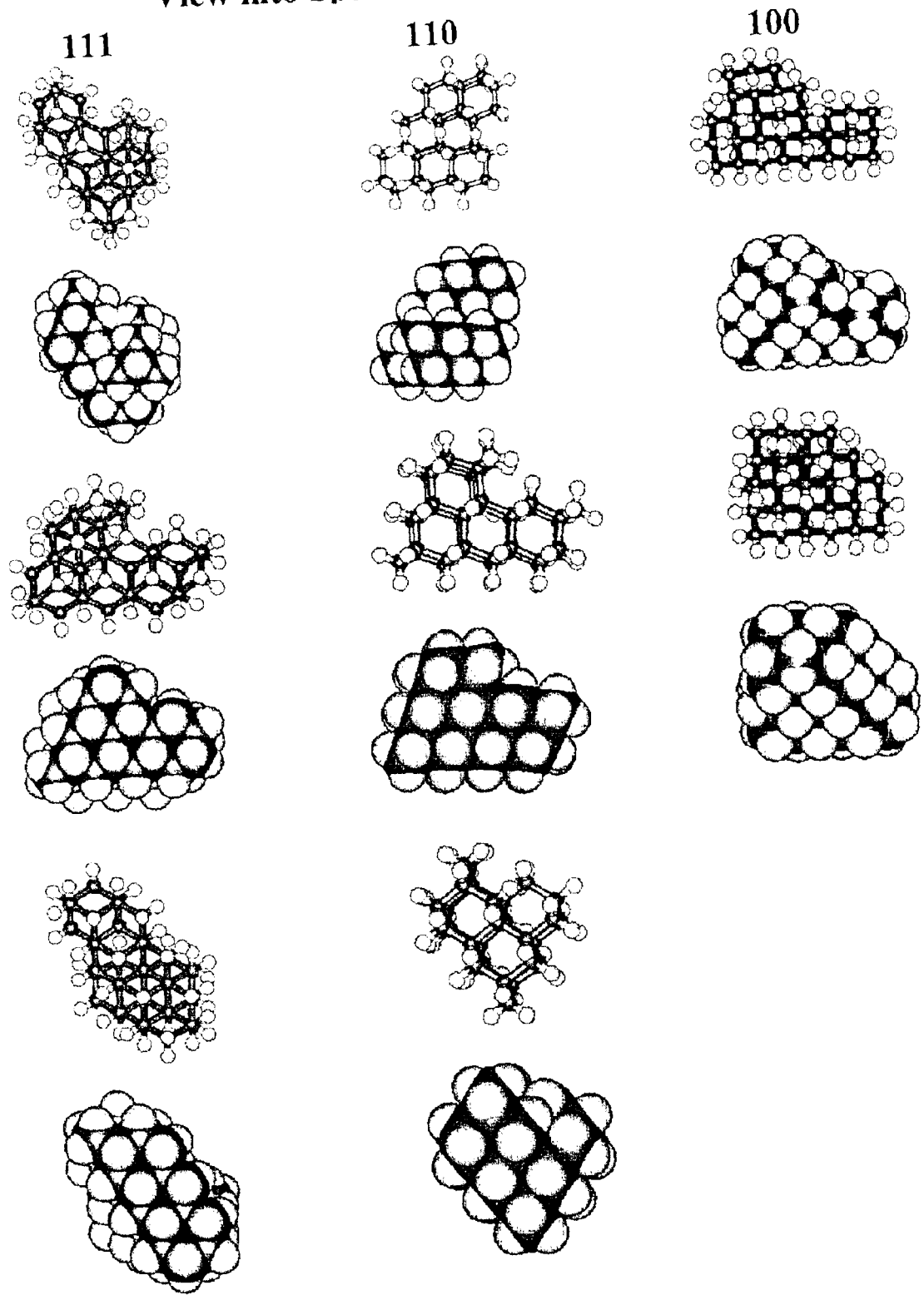
Figure 30:
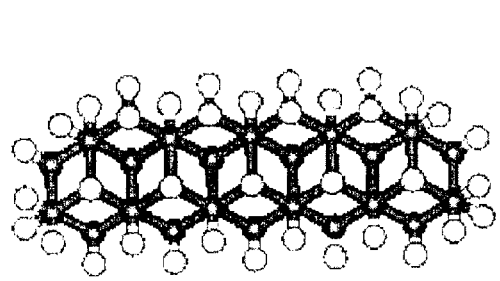
FIGS. 30–31 illustrate an example ball and stick, stick with hydrogen removed, and CPK model of a molecular formula $C_{42}H_{48}$ (molecular weight 552) nonamantane.
Figure 30:
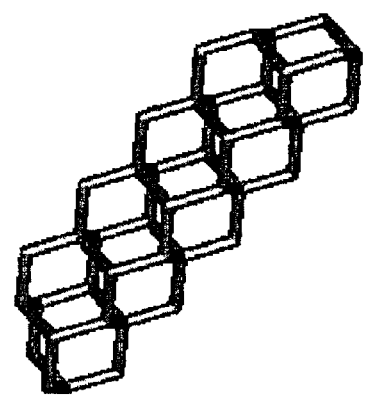
Figure 30:
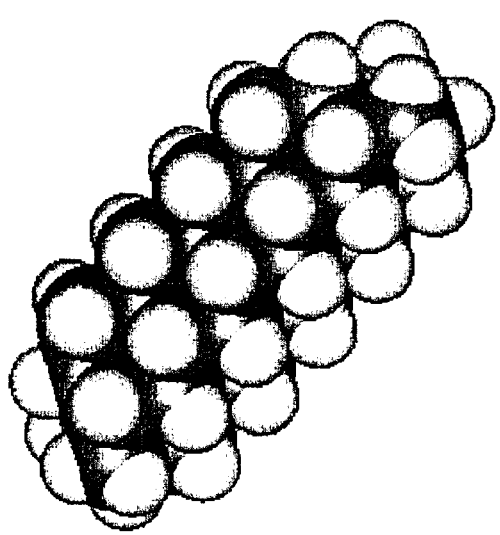
Figure 31:
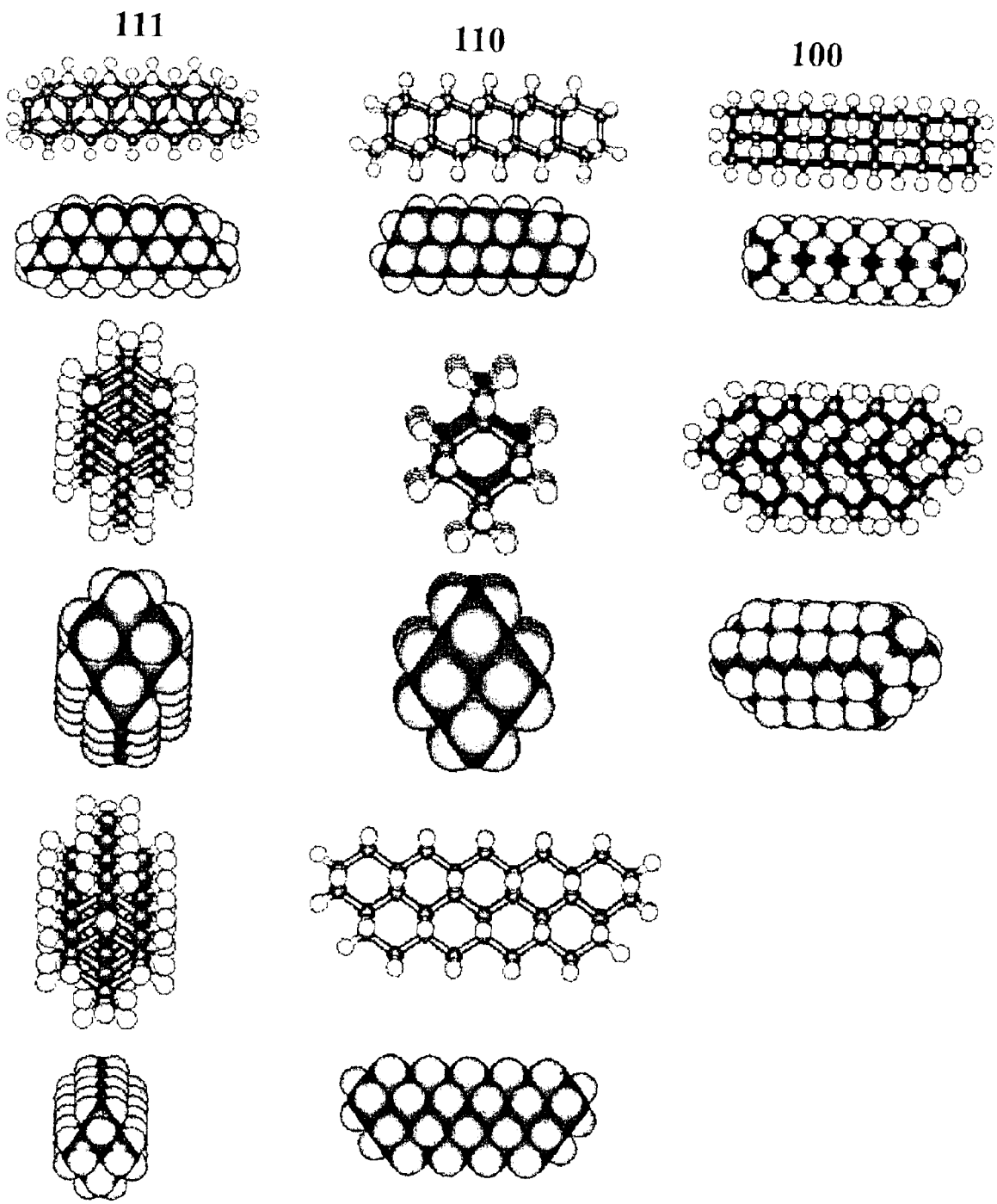

Alkylnonamantanes can be purified using methodologies described for non-alkylated nonamantanes given in Examples 3 and 4. FIGS. 19(A/B) shows methylated nonamantane in a pyrolysis product of distillate fraction #7. One type of monomethylated nonamantane has a molecular weight of 512 (yielding a mass spectrometric molecular ion of m/z 512, and show a mass spectrometric loss of the methyl group giving the m/z 497 mass spectrometric fragment ion indicative of a nonamantane moiety (FIG. 19B). More than one alkylnonamantane is present and these could be isolated using ODS or Hypercarb columns, an additional HPLC separation, or an alternative preparative GC procedure (as in Example 3) can yield high purity alkylnonamantanes

What is claimed is:

1. A composition comprising diamondoids wherein at least about 25 weight percent of the diamondoids are one or more nonamantane components.

2. A composition of claim 1 wherein from 50 to 100 weight percent of the diamondoids are one or more nonamantane components.

3. A composition of claim 1 wherein from 70 to 100 weight percent of the diamondoids are one or more nonamantane components.

4. A composition of claim 1 wherein from 95 to 100 weight percent of the diamondoids are one or more nonamantane components.

5. A composition of claim 1 wherein from 99 to 100 weight percent of the diamondoids are one or more nonamantane components.

6. The composition of any of claims 1–5, wherein the one or more nonamantane components are a single nonamantane component.

7. The composition of any of claims 1–5 wherein the one or more nonamantane components are isolated optical isomers.

8. The composition of any of claims 1–5, wherein the one or more nonamantane components are isomeric nonamantane components.

9. The composition of any of claims 1–5, wherein the one or more nonamantane component is the isomeric nonamantane component represented by the formula $C_{34}H_{36}$.

10. The composition of any of claims 1–5, wherein the one or more nonamantane components are one or more isomeric nonamantane components represented by the formula $C_{37}H_{40}$.

11. The composition of any of claims 1–5, wherein the one or more nonamantane components are one or more isomeric nonamantane components represented by the formula $C_{38}H_{42}$.

12. The composition of any of claims 1–5, wherein the one or more nonamantane components are one or more isomeric nonamantane components represented by the formula $C_{40}H_{44}$.

13. The composition of any of claims 1–5, wherein the one or more nonamantane components are one or more isomeric nonamantane components represented by the formula $C_{41}H_{46}$.

14. The composition of any of claims 1–5, wherein the one or more nonamantane components are one or more isomeric nonamantane components represented by the formula $C_{42}H_{48}$.

15. The composition of any of claims 1–5 wherein the nonamantane components comprise unsubstituted nonamantane components.

16. The composition of any of claims 1–5 wherein the nonamantane components comprise substituted nonamantane components having from 1 to 10 alkyl substituents.

17. A composition comprising at least about 10% by weight of one or more nonamantane components.

18. The composition of claim 17 containing from 50 to 100% by weight of one or more nonamantane components.

19. The composition of claim 17 containing from 70 to 100% by weight of one or more nonamantane components.

20. The composition of claim 17 containing from 95 to 100% by weight of one or more nonamantane components.

21. The composition of claim 17 containing from 99 to 100% by weight of one or more nonamantane components.

22. The composition of claims 17–21 wherein the one or more nonamantane components are a single nonamantane component.

23. The composition of claim 1, wherein the one or more nonamantane components are in crystalline form.

24. A process for recovering a composition enriched in one or more nonamantane components which process comprises:
   a. selecting a feedstock comprising recoverable amounts of nonamantane components and nonnonamantane components;
   b. removing from the feedstock a sufficient amount of nonnonamantane components having boiling points less than the lowest boiling point nonamantane component under conditions to form a treated feedstock enriched in nonamantane components which can be recovered;
   c. recovering a composition enriched in one or more nonnomantane components from said treated feedstock formed in b) above with one or more additional separation techniques selected from the group consisting of chromatographic techniques, thermal diffusion techniques, zone refining, progressive recrystallization and size separation techniques.

25. A process for recovering a composition enriched in nonamantane components which process comprises:
   a. selecting a feedstock comprising recoverable amounts of nonamantane components and nonnonamantane components including nondiamondoid components;
   b. removing from the feedstock a sufficient amount of nonnonamantane components having a boiling point less than the lowest boiling point nonamantane component under conditions to form a treated feedstock enriched in nonamantane components which can be recovered;
   c. thermally degrading said treated feedstock to pyrolyze at least a sufficient amount of nondiamondoid components therefrom under conditions to form a thermally treated feedstock retaining recoverable amounts of nonamantane;
   d. recovering a composition enriched in one or more nonamantane components from said thermally treated feedstock formed in c) above with one or more additional separation techniques selected from the group consisting of chromatographic techniques, thermal diffusion techniques, zone refining, progressive recrystallization and size separation techniques.

26. A process for recovering a composition enriched in one or more nonamantane components which process comprises:
   a. selecting a feedstock comprising recoverable amounts of nonamantane components and nonnonamantane components including nondiamondoid components;
   b. thermally degrading said feedstock to pyrolyze at least a sufficient amount of nondiamondoid components therefrom under conditions to provide a thermally treated feedstock retaining recoverable amounts of nonamantane;
   c. removing from the thermally treated feedstock a sufficient amount of nonnonamantane components having a boiling point less than the lowest boiling point of nonnomantane component under conditions to form a treated feedstock enriched in nonamantanes components which can be recovered;
   d. recovering a composition enriched in one or more nonamantane components from said treated feedstock recovered in c) above with one or more additional separation techniques selected from the group consisting of chromatographic techniques, thermal diffusion techniques, zone refining, progressive recrystallization and size separation techniques.

27. A process for recovering a composition enriched in one or more nonamantane components which process comprises:
   a. selecting a feedstock comprising recoverable amounts of nonamantane components and nonnonamantane components;
   b. fractionating the feedstock to form one or more cuts enriched in materials having boiling points in the range of from just below the boiling point of the lowest boiling nonamantane component to just above the boiling point of the highest boiling nonamantane component;
   c. recovering a composition enriched in one or more nonamantane components from said one or more cuts formed in b) above with one or more additional separation techniques selected from the group consisting of chromatographic techniques, thermal diffusion techniques, zone refining, progressive recrystallization and size separation techniques.

28. A process for recovering a composition enriched in one or more nonamantane components which process comprises:
   a. selecting a feedstock comprising recoverable amounts of nonamantane components and nonnonamantane components including nondiamondoid components;
   b. fractionating the feedstock to form one or more cuts enriched in materials having boiling points in the range of from just below the boiling point of the lowest boiling nonamantane component to just above the boiling point of the highest boiling nonamantane component;
   c. thermally degrading one or more cuts said to pyrolyze at least a sufficient amount of nondiamondoid components therefrom under conditions to form one or more thermally treated cuts retaining recoverable amounts of nonamantane;
   d. recovering a composition comprising one or more nonamantane components from one or more said thermally treated cuts formed in c) above with one or more additional separation techniques selected from the group consisting of chromatographic techniques, thermal diffusion techniques, zone refining, progressive recrystallization and size separation techniques.

29. A process for recovering a composition enriched in one or more nonamantane components which process comprises:

a. selecting a feedstock comprising recoverable amounts of nonamantane components and nonnonamantane compounds including nondiamondoid components;
b. thermally degrading said feedstock to pyrolyze at least a sufficient amount of nondiamondoid components therefrom under conditions to provide a thermally treated feedstock retaining recoverable amounts of nonamantane;
c. fractionating the thermally treated feedstock to form one or more cuts enriched in materials having boiling points in the range of from just below the boiling point of the lowest boiling nonamantane component to just above the boiling point of the highest boiling nonamantane component;
d. recovering a composition enriched in one or more nonamantane components from one or more cuts formed c) above with one or more additional separation techniques selected from the group consisting of chromatographic techniques, thermal diffusion techniques, zone refining, progressive recrystallization and size separation techniques.

30. The process according to any of claims 27–29 wherein said boiling point range is a range having atmospheric equivalents of between about 380 to about 630° C.

31. The process according to any of claims 24–29 wherein said separation technique is a chromatographic technique.

32. The process according to claim 31 wherein said chromatographic technique is selected from the group consisting of liquid chromatography, preparative gas chromatography and high performance liquid chromatography.

33. The process according to claim 31 wherein said additional separation technique is high performance liquid chromatography comprising one or more high performance liquid chromatography columns.

34. The process according to claim 33 wherein the high performance liquid chromatography columns are selected to have a different specificity to the nonamantane components.

35. A product prepared by the process of claim 24.

36. A product prepared by the process of claim 25.

37. A product prepared by the process of claim 26.

38. A product prepared by the process of claim 27.

39. A product prepared by the process of claim 28.

40. A product prepared by the process of claim 29.

* * * * *